(12) United States Patent
Horwitz et al.

(10) Patent No.: US 8,383,132 B2
(45) Date of Patent: *Feb. 26, 2013

(54) IMMUNOSTIMULATORY RECOMBINANT INTRACELLULAR PATHOGEN IMMUNOGENIC COMPOSITIONS AND METHODS OF USE

(75) Inventors: Marcus A. Horwitz, Los Angeles, CA (US); Michael Tullius, Encino, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/986,598

(22) Filed: Jan. 7, 2011

(65) Prior Publication Data
US 2011/0129492 A1    Jun. 2, 2011

Related U.S. Application Data

(63) Continuation-in-part of application No. 12/296,666, filed as application No. PCT/US2007/066350 on Apr. 10, 2007, now Pat. No. 8,287,879, which is a continuation-in-part of application No. 10/595,385, filed as application No. PCT/US2004/034206 on Oct. 15, 2004, now Pat. No. 7,622,107.

(60) Provisional application No. 60/744,557, filed on Apr. 10, 2006, provisional application No. 60/512,565, filed on Oct. 16, 2003.

(51) Int. Cl.
 *A61K 39/04* (2006.01)
 *A61K 48/00* (2006.01)
 *C07H 21/04* (2006.01)

(52) U.S. Cl. .............. 424/248.1; 424/93.2; 536/23.1; 536/23.7

(58) Field of Classification Search .................. None
See application file for complete search history.

(56) References Cited

U.S. PATENT DOCUMENTS

| | | | |
|---|---|---|---|
| 5,504,005 A | 4/1996 | Bloom et al. | |
| 5,583,038 A | 12/1996 | Stover | |
| 5,591,632 A | 1/1997 | O'Donnell et al. | |
| 5,679,515 A | 10/1997 | Stover et al. | |
| 5,700,683 A | 12/1997 | Stover et al. | |
| 5,736,367 A | 4/1998 | Haun et al. | |
| 5,776,465 A | 7/1998 | O'Donnell et al. | |
| 5,807,723 A | 9/1998 | Aldovini et al. | |
| 5,830,475 A | 11/1998 | Aldovini et al. | |
| 5,854,055 A | 12/1998 | Bloom et al. | |
| 5,866,403 A | 2/1999 | Aldovini et al. | |
| 5,869,057 A | 2/1999 | Rock | |
| 6,015,696 A | 1/2000 | Yamada et al. | |
| 6,467,967 B2 | 10/2002 | Dicke et al. | |
| 6,471,967 B1 | 10/2002 | Horwitz et al. | |
| 6,924,118 B2 | 8/2005 | Horwitz et al. | |
| 7,288,261 B2 | 10/2007 | Orme et al. | |
| 2002/0081664 A1* | 6/2002 | Lo et al. ................... 435/69.5 |
| 2004/0009184 A1 | 1/2004 | Horwitz et al. | |
| 2004/0228873 A1 | 11/2004 | Horwitz et al. | |

FOREIGN PATENT DOCUMENTS

| | | |
|---|---|---|
| WO | 88/06626 | 9/1988 |
| WO | WO01/78774 A2 | 10/2001 |
| WO | WO 01/78774 A2 * | 10/2001 |
| WO | 2004/031356 | 4/2004 |
| WO | 2005/037222 | 4/2005 |

OTHER PUBLICATIONS

Murray et al (Proc. Natl. Acad. Sci, vol. 93, p. 934-939, Jan. 1996).*
Harth et al (Infection and Immunity, vol. 65, No. 6, Jun. 1997, p. 2321-2328).*
O'Donnell et al (Infection and Immunity, vol. 62, No. 6, Jun. 1994, p. 2508-2514).*
Young et al (International Immunology, vol. 14, No. 7, pp. 793-800).*
Anderson, Daniel H., et al., "An Interfacial Mechanism and a Class of Inhibitors Inferred from Two crystal Structures of the *Mycobacterium tuberculosis* 30 kDa Major Secretory Protein (Antigen 85B), a Mycolyl Transferase", J. Mol. Biol., vool. 307, 2001, pp. 671-681.
Bachrach, Gilad, et al., "A new single-copy mycobacterial plasmid, pMF1, from *Mycobacterium fortuitum* which is compatible with the pAL5000 replicon", Microbiology, vol. 146, 2000, pp. 297-303.
Baldwin, Susan L., et al., "Evaluation of New Vaccines in the Mouse and Guinea Pig Model of Tuberculosis", Infection and Immunity, vol. 66, No. 6, Jun. 1998, pp. 2951-2959.
Bardarov, Stoyan, et al., "Specialized transduction: an efficient method for generating marked and unmared tarteted gene disruptions in *Mycobacterium tuberculosis, M. bovis* BCG and *M. smegmatis*", Microbiology, vol. 148, 2002, pp. 3007-3017.
Belisle et al. "Role of the major antigen of *Mycobacterium tuberculosis* in cell wall biogenesis." Science 276: 1420-1422, 1997.
Brooks et al. "Boosting vaccine for tuberculosis." Infect. Immun, 69:2714-17, 2001.
Chambers et al. "Identification of a *Mycobacterium bovis* BCG Auxotrophic Mutant that Protects Guinea Pigs against *M. bovis* and Hematogenous Spread of *Mycobacterium tuberculosis* without Sensitization to Tuberculin." Infection and Immunity, Dec. 2000, p. 7094-7099, vol. 68, No. 12.
Cirillo et al., "Bacterial Vaccine Vectors and Bacillus Calmette-Guerin", Clinical Infectious Diseases, 20:1001-9 (1995).
Fan, Xiong-lin, et al., Cloning and expression of the fusion protein of interleukin-2 and ESAT6 in *Mycobacterium bovis* Vacillus Calmette Guerin strain, Chinese Medical Journal (English Edition), vol. 118, No. 9, May 2005, pp. 762-765.
Fan, Xiong-lin, et al., "Immunological Properties of Recombinant *Mycobacterium vovis* Bacillus Calmette-Guerin Strain Expressing Fusion Protein IL-2-ESAT-6", ACTA Biochimica Et Biophysica Sinica, vol. 38, No. 10, Oct. 2006, pp. 683-690.

(Continued)

*Primary Examiner* — Rodney P. Swartz
(74) *Attorney, Agent, or Firm* — K&L Gates LLP; Louis C. Cullman; Michelle Glasky Bergman

(57) ABSTRACT

Immunogenic compositions comprising recombinant intracellular pathogens that have been transformed to express recombinant immunogenic antigens of the same or other intracellular pathogens and immunostimulatory molecules are provided. Exemplary immunogenic compositions include, but are not limited to, recombinant BCG expressing *Mycobacteria* major extracellular proteins and immunostimulatory molecules.

20 Claims, 13 Drawing Sheets

OTHER PUBLICATIONS

Figure 1:
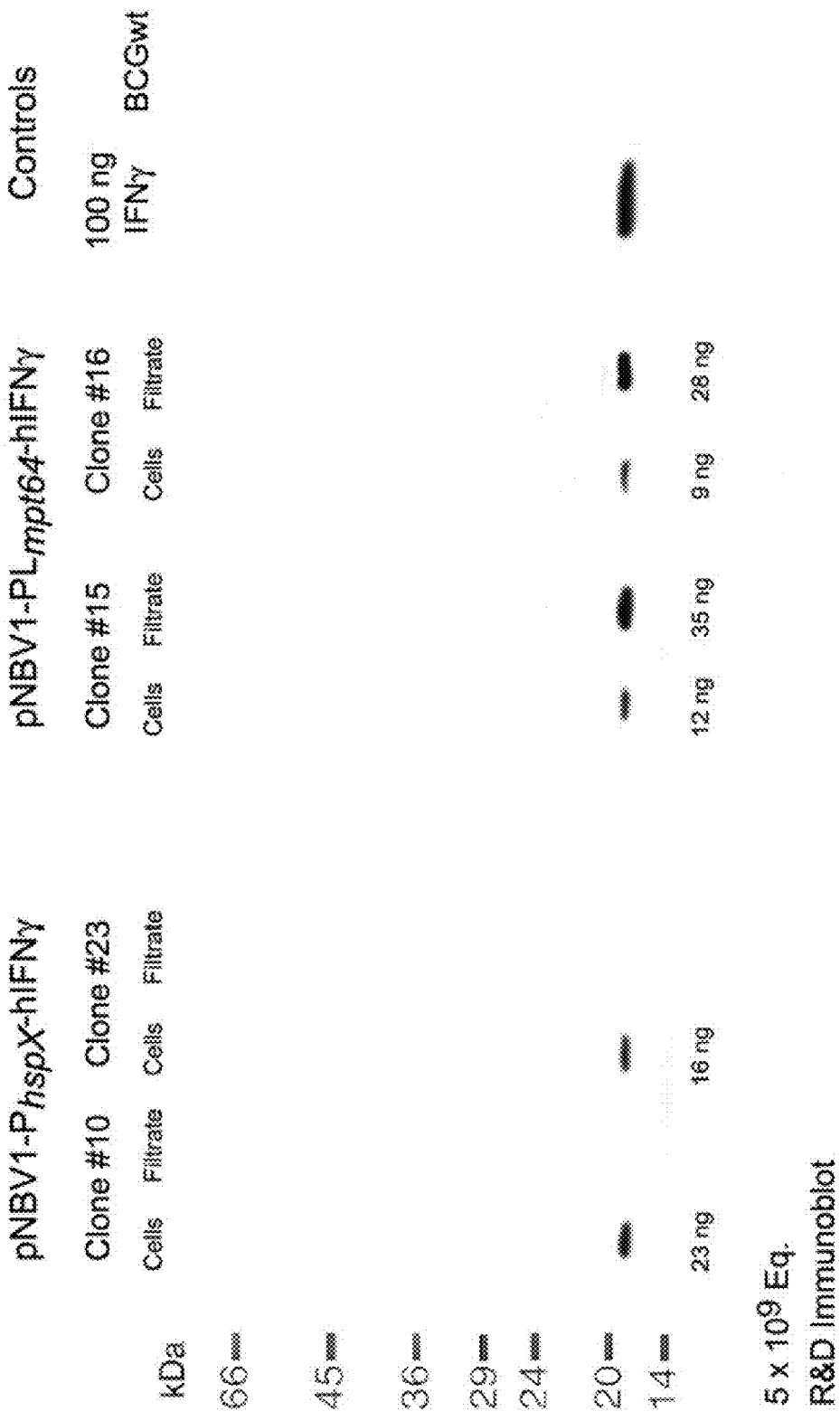

Fuerst et al., "Development and Analysis of Recombinant BCG Vector Systems", AIDS Research and Human Retroviruses, 8:1451-5 (1992).

Hanson et al., "Efficacy and Safety of Live Recombinant BCG Vaccines", Dev. Biol. Stand., 84:229-36 (1995).

Harth et al., "Novel Insights into the Genetics, Biochemistry, and Immunocytochemistry of the 30-Kilodalton Major Extracellular Protein of *Mycobacterium tuberculosis*", Infection and Immunity, 64:3038-47 (1996).

Harth et al., "High-Level Heterologous Expression and Secretion in Rapidly Growing Nonpathogenic Mycobacteria of Four Major *Mycobacterium tuberculosis* Extracellular Proteins Considered to be Leading Vaccine Candidates and Drug Targets", Infection and Immunity, 65:2321-8 (1997).

Harth, Gunter, et al., "A two-plasmid system for stable, selective-pressure-independent expression of multiple extracellular proteins in mycobacteria", Microbiology, vol. 150, No. Part 7, Jul. 2004, pp. 2143-2151.

Herrmann, J.L., et al., "Bacterial glycoproteins: a link between glycosylation and proteolytic cleavage of a 19 KDa antigen from Mycobactyerium tuberculosis", the EMBO Journal, vol. 15, No. 14, 1996, pp. 3547-3554.

Horwtiz et al., "Protective immunity against tuberculosis induced by vaccination with major extracellular proteins of *Mycobacterium tuberculosis*." Proc. Natl. Acad. Sci. USA 92:1530-1534, 1995.

Horwtiz et al., "Recombinant Bacillus Calmette-Guerin (BCG) Vaccines Expressing the *Mycobacterium tuberculosis* 30-kDa Major Secretory Protein Induce Greater Protective Immunity Against Tuberculosis Than Conventional BCG Vaccines in a Highly Susceptible Animal Model", PNAS, 97:13853-8 (2000).

Howard, Nathan S., et al., "Color selection with ahygromycin-resistance-based *Escherichia coli*mycobacterial shuttle vector*", Gene, vol. 166, 1998, pp. 181-182.

Langermann et al., "Protective Humoral Response Against Pneumococcal Infection in Mice Elicited by Recombinant Bacille Calmette-Guerin Vaccines Expressing Pneumococcal Surface Protein A", J Exp Med., 180:2277-86 (1994).

Langermann et al., "Systemic and Mucosal Immunity Induced by BCG Vector Expressing Outer-Surface Protein A of *Borrelia burgdorferi*", Nature, 372:552-5 (1994).

Lee et al., "T-Cell Epitope Mapping of the Three Most Abundant Extracellular Proteins of *Mycobacterium tuberculosis* in Outbred Guinea Pigs", Infection and Immunity, 67:2665-70 (1999).

Martin, Ela, et al., "The combination of plasmid interleukin-12 with a single DNA vacine is more effective than *Mycobacterium bovis* (bacille Calmette-Guerin) in protecting against systemic *Mycobacterium avium* infection", Immunology, vol. 109, No. 2, Jun. 2003, pp. 308-314.

Murray, Pete J., et al., "Manipulation and protentiation of antimycobacterial immunity using recombinant bacille Calmette-Guerin strains that secrete cytokines", Proceedings of the National Academy of Sciences of the United States of America, vol. 93, No. 2, 1996, pp. 934-939.

Naito et al., "The Antigen 85 Complex Vaccine Against Experimental *Mycobacterium leprae* Infection in Mice", Vaccine, 19:795-8 (2000).

O'Donnell, Michael A., et al., "Recombinant *Nycobacterium bovis* BCG Secreting functional Interleukin-2 Enhances Gamma Interferon Production by Splenocytes", Infection and Immunity, vol. 62, No. 6, Jun. 1994, pp. 2508-2514.

Ohara et al., "Characterization of the Transcriptional Initiation Regions of Genes for the Major Secreted Protein Antigens 85C and MPB51 of Mycobacerium bovis BCG", Microbial Pathogenesis, 23:303-10, (1997).

Ohara et al., "Inhibition of Multiplication of *Mycobacterium leprae* in Mouse Foot Pads by Recombinant Bacillus Calmette-Guerin (BCG)", Vaccine, 19:1294-7 (2000).

Smith et al. "Characterization of Auxotrophic Mutants of *Mycobacterium tuberculosis* and Their Potential as Vaccine Candidates." Infection and Immunity, Feb. 2001, p. 1142-1150, vol. 69, No. 2.

Stover et al., "New Use of BCG for Recombinant Vaccines", Nature, 351:456-60 (1991).

Stover et al., "Use of Recombinant BCG as a Vaccine Delivery Vehicle", Advances in Experimental Medicine and Biology, 327: 175-82 (1992).

Stover et al., "Protective Immunity Elicited by Recombinant Bacille Calmette-Guerin (BCG) Expressing Outer Surface Protein A (OspA) Lipoprotein: A Candidate Lyme Disease Vaccine", J. Exp. Med., 178:197-209 (1993).

Stover et al., "Protective Immunity Elicited by rBCG Vaccines", Dev. Biol. Stand., 82:163-70 (1994).

Tullius et al. "High Extracellular Levels of *Mycobacterium tuberculosis* Glutamine Synthetase and Superoxide Dismutase in Actively Growing Cultures Are Due to High Expression and Extracellular Stability Rather than to a Protein-Specific Export Mechanism." Infection and Immunity, Oct. 2001, p. 6348-6363, vol. 69, No. 10.

Walter, Mark R., et al., "Crystal structure of a complex between interferon-y and its soluble high-affinity receptor", Nature, vol. 376, Jul. 20, 1995, pp. 230-235.

Yasutomi et al., "Immunization with Recombinant BCG-SIV Elicits SIV-Specific Cytotoxic T. Lymphocytes in Rhesus Monkeys", The Journal of Immunology, 150:3101-7 (1993).

Young et al. "IL-2-secreting recombinant bacillus Calmette Guerin can overcome a Type 2 immune response and corticosteroid-induced immunosuppression to elicit a Tye 1 immune response." International Immunology, vol. 14, No. 7, pp. 293-800, 2002.

\* cited by examiner

FIG. 7 rBCG Expressing *M. tuberculosis* 30 kDa Protein and Soluble Human IL4 Receptor

FIG. 13

FIG. 14

SEQUENCE LISTING

<160> NUMBER OF SEQ ID NOS: 4

<210> SEQ ID NO 1
<211> LENGTH: 32
<212> TYPE: PRT
<213> ORGANISM: Mycobacterium tuberculosis

```
<400> SEQUENCE: 1

Met Thr Arg Arg Gln Phe Phe Ala Lys Ala Ala Ala Ala Thr Thr Ala
1               5                   10                  15

Gly Ala Phe Met Ser Leu Ala Gly Pro Ile Ile Glu Lys Ala Tyr Gly
                20                  25                  30

<210> SEQ ID NO 2
<211> LENGTH: 54
<212> TYPE: PRT
<213> ORGANISM: Bacillus subtilis

<400> SEQUENCE: 2

Met Ala Tyr Asp Ser Arg Phe Asp Glu Trp Val Gln Lys Leu Lys Glu
1               5                   10                  15

Glu Ser Phe Gln Asn Asn Thr Phe Asp Arg Arg Lys Phe Ile Gln Gly
                20                  25                  30

Ala Gly Lys Ile Ala Gly Leu Ser Leu Gly Leu Thr Ile Ala Gln Ser
            35                  40                  45

Val Gly Ala Phe Glu Val
        50

<210> SEQ ID NO 3
<211> LENGTH: 39
<212> TYPE: PRT
<213> ORGANISM: Escherichia coli

<400> SEQUENCE: 3

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
                20                  25                  30

Thr Pro Arg Arg Ala Thr Ala
            35

<210> SEQ ID NO 4
<211> LENGTH: 17
<212> TYPE: PRT
<213> ORGANISM: Homo sapiens

<400> SEQUENCE: 4

Pro Val Pro Ser Thr Pro Pro Thr Pro Ser Pro Ser Thr Pro Thr Pro
1               5                   10                  15

Ser
```

IMMUNOSTIMULATORY RECOMBINANT INTRACELLULAR PATHOGEN IMMUNOGENIC COMPOSITIONS AND METHODS OF USE

CROSS REFERENCE TO RELATED APPLICATIONS

This application is a continuation-in-part of co-pending U.S. patent application Ser. No. 12/296,666 filed Oct. 9, 2008, which claims the benefit under 35 U.S.C. §371 to PCT/US2007/66350 filed Apr. 10, 2007, which claims the benefit under 35 U.S.C. §119(e) to U.S. Provisional Patent Application No. 60/744,557 filed Apr. 10, 2006 and is a continuation-in-part of co-pending U.S. patent application Ser. No. 10/595,385 filed Apr. 13, 2006 which claims the benefit under 35 U.S.C. §371 to PCT/US04/34206 filed Oct. 15, 2004 and which in turn claims the benefit under 35 U.S.C. §119(e) to U.S. Patent Application No. 60/512,565 filed Oct. 16, 2003. The entire contents of each of these applications are incorporated by reference herein.

STATEMENT REGARDING FEDERALLY SPONSORED RESEARCH

This invention was made with Government support under Grant No. AI31338 and AI068413 awarded by the Department of Health and Human Services. The Government has certain rights in this invention.

FIELD OF THE INVENTION

The present invention generally relates to immunogenic compositions derived from recombinant intracellular pathogenic bacteria. Moreover, the immunogenic compositions of the present invention comprise recombinant *Mycobacteria* that secrete pathogen intracellular proteins alone or in combination with host immunostimulatory molecules. The immunogenic compositions of the present invention are useful in inducing immune responses in hosts.

BACKGROUND OF THE INVENTION

It has long been recognized that parasitic microorganisms possess the ability to infect animals thereby causing disease and often death. Pathogenic agents have been a leading cause of death throughout history and continue to inflict immense suffering. Though the last hundred years have seen dramatic advances in the prevention and treatment of many infectious diseases, complicated host-parasite interactions still limit the universal effectiveness of therapeutic measures. Difficulties in countering the sophisticated invasive mechanisms displayed by many pathogenic organisms are evidenced by the resurgence of various diseases such as tuberculosis, as well as the appearance of numerous drug resistant strains of bacteria and viruses.

Among those pathogenic agents of major epidemiological concern, intracellular bacteria have proven to be particularly intractable in the face of therapeutic or prophylactic measures. Intracellular bacteria, including the genus *Mycobacterium*, complete all or part of their lifecycle within the cells of the infected host organism rather than extracellularly. Around the world, intracellular bacteria are responsible for untold suffering and millions of deaths each year. Tuberculosis is the leading cause of death from a single disease agent worldwide, with 8 million new cases and 2 million deaths annually. In addition, intracellular bacteria are responsible for millions of cases of leprosy. Other debilitating diseases transmitted by intracellular agents include cutaneous and visceral leishmaniasis, American trypanosomiasis (Chagas disease), listeriosis, toxoplasmosis, histoplasmosis, trachoma, psittacosis, Q-fever, legionellosis, anthrax and tularemia.

Currently it is believed that approximately one-third of the world's population is infected by *Mycobacterium tuberculosis* resulting in millions of cases of pulmonary tuberculosis annually. More specifically, human pulmonary tuberculosis primarily caused by *M. tuberculosis* is a major cause of death in developing countries. *Mycobacterium tuberculosis* is capable of surviving inside macrophages and monocytes, and therefore may produce a chronic intracellular infection. *Mycobacterium tuberculosis* is relatively successful in evading the normal defenses of the host organism by concealing itself within the cells primarily responsible for the detection of foreign elements and subsequent activation of the immune system. Moreover, many of the front-line chemotherapeutic agents used to treat tuberculosis have relatively low activity against intracellular organisms as compared to extracellular forms. These same pathogenic characteristics have heretofore limited the effectiveness of immunotherapeutic agents or immunogenic compositions against tubercular infections.

Recently, tuberculosis resistance to one or more drugs was reported in 36 of the 50 United States. In New York City, one-third of all cases tested was resistant to one or more major drugs. Though non-resistant tuberculosis can be cured with a long course of antibiotics, the outlook regarding drug resistant strains is bleak. Patients infected with strains resistant to two or more major antibiotics have a fatality rate of around 50%. Accordingly, safe and effective immunogenic compositions against multi-drug resistant strains of *M. tuberculosis* are sorely needed.

Initial infections of *M. tuberculosis* almost always occur through the inhalation of aerosolized particles as the pathogen can remain viable for weeks or months in moist or dry sputum. Although the primary site of the infection is in the lungs, the organism can also cause infection of nearly any organ including, but not limited to, the bones, spleen, kidney, meninges and skin. Depending on the virulence of the particular strain and the resistance of the host, the infection and corresponding damage to the tissue may be minor or extensive. In the case of humans, the initial infection is controlled in the majority of individuals exposed to virulent strains of the bacteria. The development of acquired immunity following the initial challenge reduces bacterial proliferation thereby allowing lesions to heal and leaving the subject largely asymptomatic.

When *M. tuberculosis* is not controlled by the infected subject it often results in the extensive degradation of lung tissue. In susceptible individuals, lesions are usually formed in the lung as the tubercle bacilli reproduce within alveolar or pulmonary macrophages. As the organisms multiply, they may spread through the lymphatic system to distal lymph nodes and through the blood stream to the lung apices, bone marrow, kidney and meninges surrounding the brain. Primarily as the result of cell-mediated hypersensitivity responses, characteristic granulomatous lesions or tubercles are produced in proportion to the severity of the infection. These lesions consist of epithelioid cells bordered by monocytes, lymphocytes and fibroblasts. In most instances a lesion or tubercle eventually becomes necrotic and undergoes caseation (conversion of affected tissues into a soft cheesy substance).

While *M. tuberculosis* is a significant pathogen, other species of the genus *Mycobacterium* also cause disease in animals including man and are clearly within the scope of the present invention. For example, *M. bovis* is closely related to *M. tuberculosis* and is responsible for tubercular infections in domestic animals such as cattle, pigs, sheep, horses, dogs and cats. Further, *M. bovis* may infect humans via the intestinal tract, typically from the ingestion of raw milk. The localized intestinal infection eventually spreads to the respiratory tract and is followed shortly by the classic symptoms of tuberculosis. Another important pathogenic species of the genus *Mycobacterium* is *M. leprae* that causes millions of cases of the ancient disease leprosy. Other species of this genus which cause disease in animals and man include *M. kansasii, M. avium intracellulare, M. fortuitum, M. marinum, M. chelonei,* and *M. scrofulaceum*. The pathogenic mycobacterial species frequently exhibit a high degree of homology in their respective DNA and corresponding protein sequences and some species, such as *M. tuberculosis* and *M. bovis*, are highly related.

Attempts to eradicate tuberculosis using immunogenic compositions was initiated in 1921 after Calmette and Guérin successfully attenuated a virulent strain of *M. bovis* at the Institut Pasteur in Lille, France. This attenuated *M. bovis* became known as the Bacille Calmette Guérin, or BCG for short. Ninety years later, immunogenic compositions derived from BCG remain the only prophylactic therapy for tuberculosis currently in use. In fact, all BCG immunogenic compositions available today are derived from the original strain of *M. bovis* developed by Calmette and Guérin at the Institut Pasteur.

The World Health Organization considers the BCG immunogenic compositions an essential factor in reducing tuberculosis worldwide, especially in developing nations. In theory, the BCG immunogenic composition confers cell-mediated immunity against an attenuated mycobacterium that is immunologically related to *M. tuberculosis*. The resulting immune response should inhibit primary tuberculosis. Thus, if primary tuberculosis is inhibited, latent infections cannot occur and disease reactivation is avoided.

Current BCG immunogenic compositions are provided as lyphophilized cultures that are re-hydrated with sterile diluent immediately before administration. The BCG immunogenic composition is given at birth, in infancy, or in early childhood in countries that practice BCG vaccination, including developing and developed countries. Adult visitors to endemic regions who may have been exposed to high doses of infectious *Mycobacteria* may receive BCG as a prophylactic providing they are skin test non-reactive. Adverse reactions to the immunogenic composition are rare and are generally limited to skin ulcerations and lymphadenitis near the injection site. However, in spite of these rare adverse reactions, the BCG immunogenic composition has an unparalleled history of safety with over four billion doses having been administered worldwide since 1930.

However, the unparalleled safety of traditional BCG immunogenic compositions is coming under increased scrutiny and has created a paradox for healthcare practitioners. The population segments most susceptible to mycobacterial infections are the immunocompromised and immunosuppressed. Persons suffering from early or late-stage HIV infections are particularly susceptible to infection. Unfortunately, many persons in the early-stage of HIV infection are unaware of their immune status. It is likely that these individuals may voluntarily undergo immunization using a live attenuated immunogenic composition such as BCG without being forewarned of their unique risks. Moreover, other mildly immunocompromised or immunosuppressed individuals may also unwittingly undergo immunization with BCG hoping to avoid mycobacterial disease. Therefore, safer, more efficacious BCG and BCG-like immunogenic compositions are desirable.

Recently, significant attention has been focused on using transformed BCG strains to produce immunogenic compositions that express various cell-associated antigens. For example, C. K. Stover, et al. have reported a Lyme Disease immunogenic composition using a recombinant BCG (rBCG) that expresses the membrane associated lipoprotein OspA of *Borrelia burgdorferi*. Similarly, the same author has also produced a rBCG immunogenic composition expressing a pneumococcal surface protein (PsPA) of *Streptococcus pneumoniae*. (Stover C K, Bansal G P, Langerman S, and Hanson M S. 1994. Protective immunity elicited by rBCG immunogenic compositions. In: Brown F. (ed): Recombinant Vectors in Immunogenic composition Development. Dev Biol Stand. Dasel, Karger, Vol. 82:163-170)

U.S. Pat. No. 5,504,005 (the "'005" patent") and U.S. Pat. No. 5,854,055 (the "'055 patent") both issued to B. R. Bloom et al., disclose theoretical rBCG vectors expressing a wide range of cell associated fusion proteins from numerous species of microorganisms. The theoretical vectors described in these patents are either directed to cell-associated fusion proteins, as opposed to extracellular non-fusion protein antigens, and/or the rBCG is hypothetically expressing fusion proteins from distantly related species.

Furthermore, neither the '005 nor the '055 patent disclose animal model safety testing, immune response development or protective immunity in an animal system that closely emulates human disease. In addition, only theoretical rBCG vectors expressing *M. tuberculosis* fusion proteins are disclosed in the '005 and '055 patents; no actual immunogenic compositions are enabled. Those immunogenic composition models for *M. tuberculosis* that are disclosed are directed to cell-associated heat shock fusion proteins, not extracellular non-fusion proteins.

U.S. Pat. No. 5,830,475 (the "'475 patent") also discloses theoretical mycobacterial immunogenic compositions used to express fusion proteins. The immunogenic compositions disclosed are intended to elicit immune responses in non-human animals for the purpose of producing antibodies thereto and not shown to prevent intracellular pathogen diseases in mammals. Moreover, the '475 patent does not disclose recombinant immunogenic compositions that use protein specific promoters to express extracellular non-fusion proteins.

U.S. Pat. No. 6,467,967 claims immunogenic compositions comprising a recombinant BCG having an extrachromosomal nucleic acid sequence comprising a gene encoding a *M. tuberculosis* 30 kDa major extracellular protein (also known as Antigen 85B), wherein the *M. tuberculosis* 30 kDa major extracellular protein is over-expressed and secreted. Moreover, U.S. Pat. No. 6,924,118 claims additional recombinant BCG that over-express other *M. tuberculosis* major extracellular proteins.

Therefore, there remains a need for recombinant intracellular pathogen immunogenic compositions that induce protective immune responses.

SUMMARY OF THE INVENTION

The present invention provides methods for producing recombinant immunogenic compositions for preventing or treating diseases of intracellular pathogens in humans and animals, immunogenic compositions against diseases of intracellular pathogens in humans and animals, and a new approach to producing immunogenic compositions against tuberculosis, leprosy, other mycobacterial diseases, and other intracellular pathogens.

In one embodiment, an immunogenic composition is provided comprising a recombinant Bacille Calmette Guérin (rBCG) expressing a 30 kDa *Mycobacteria* major extracellular protein, wherein the 30 kDa *Mycobacteria* major extracellular protein is over-expressed and secreted; and interferon gamma, wherein the interferon gamma is expressed from an extrachromosomal nucleic acid.

In another embodiment, at least one of the at least one *Mycobacteria* major extracellular proteins are expressed on one or more extrachromosomal nucleic acid sequences. In another embodiment, at least one of the cytokines are expressed on one or more extrachromosomal nucleic acid sequences. In yet another embodiment, the at least one *Mycobacteria* major extracellular proteins and the at least one cytokine are expressed from different extrachromosomal nucleic acid sequences. In yet another embodiment, the at least one *Mycobacteria* major extracellular proteins and the at least one cytokine are expressed from the same extrachromosomal nucleic acid sequence.

In another embodiment, at least one of the at least one *Mycobacteria* major extracellular proteins are integrated into the rBCG genome under the control of a strong promoter and over-expressed. In another embodiment, at least one of said at least one cytokine are integrated into the rBCG genome under the control of a strong promoter and expressed. In another embodiment, the at least one *Mycobacteria* major extracellular proteins and the at least one cytokine are integrated into the rBCG genome under the control of a strong promoter and over-expressed.

In another embodiment, at least one *Mycobacteria* major extracellular protein is integrated into the rBCG genome under the control of a strong promoter and over-expressed and at least one of the cytokines are expressed on one or more extrachromosomal nucleic acid sequences.

In yet another embodiment, the at least one major extracellular protein is a non-fusion protein. In another embodiment, the at least one major extracellular protein is a fusion protein.

In another embodiment, the *Mycobacteria* major extracellular protein is from a species of *Mycobacterium* selected from the group consisting of *Mycobacterium tuberculosis, Mycobacterium bovis, Mycobacterium leprae*, and *Mycobacterium avium intracellulare.*

In another embodiment, the *Mycobacteria* major extracellular protein is over-expressed and secreted such that a protective immune response is induced in a host.

In another embodiment, the immunogenic composition further expresses at least one additional *Mycobacteria* major extracellular protein selected from the group consisting of 12 kDa protein, 14 kDa protein, 16 kDa protein, 23.5 kDa protein, 24 kDa protein, 32A kDa protein, 32B kDa protein, 45 kDa protein, 58 kDa protein, 71 kDa protein, 80 kDa protein, and 110 KD protein.

In another embodiment, the interferon gamma is a covalent dimer comprising one copy of an interferon gamma gene linked to a 19 amino acid peptide linker which is in turn linked to a second copy of an interferon gamma gene. In another embodiment, the interferon gamma is expressed in the absence of a signal peptide.

In another embodiment, the rBCG is growth-regulatable. In yet another embodiment, the rBCG is siderophore-deficient.

In one embodiment, a method is provided of inducing a protective immune response to *Mycobacteria tuberculosis* in a host comprising administering the immunogenic composition to said host, wherein a protective immune response to *M. tuberculosis* is induced in said host. In another embodiment, the host has previously been immunized with a BCG-containing vaccine.

BRIEF DESCRIPTION OF THE DRAWINGS

FIG. 1 depicts intracellular expression of human interferon gamma (hINFγ) by rBCG PhspX-hINFγ Tice and intracellular and extracellular expression of human interferon gamma by rBCG PLmpt64-hINFγ Tice.

FIG. 2 depicts expression of recombinant human soluble IL-4 receptor (N-terminal 207 amino acids) by rBCG PLmpt64-hsIL4R Tice.

FIG. 3 depicts expression and secretion of the *M. tuberculosis* 30 kDa major secretory protein and hINFγ by rBCG30/hINFγ (pSMT3-MTB30; pGB9.2-hINFγ) Tice.

FIG. 4 depicts expression and secretion of the *M. tuberculosis* 30 kDa major secretory protein and human granulocyte-macrophage colony stimulating factor by rBCG30/hGM-CSF(pSMT3-MTB30; pGB9.2-hGM-CSF) Tice; expression and secretion of the *M. tuberculosis* 30 kDa major secretory protein and human interleukin 2 (IL-2) by rBCG30/hIL-2 (pSMT3-MTB30; pGB9.2-hIL-2) Tice; and expression and secretion of the *M. tuberculosis* 30 kDa major secretory protein and human interleukin 12 (IL-12) by rBCG30/hIL-12 (pSMT3-MTB30; pGB9.2-hIL-12) Tice.

FIG. 5 depicts expression and secretion of the *M. tuberculosis* 30 kDa major secretory protein and guinea pig INFγ by rBCG30/gpINFγ (pSMT3-MTB30, pGB9.2-gpINFγ).

FIG. 6 depicts expression and secretion of *M. tuberculosis* 30 kDa major secretory protein and bovine INFγ by rBCG30/bINFγ (pSMT3-MTB30, pGB9.2-bINFγ).

FIG. 7 depicts expression and secretion of *M. tuberculosis* 30 kDa major secretory protein and human soluble IL-4 receptor by rBCG30/hsIL-4R (pSMT3-MTB30; pGB9.2-hsIL-4R) Tice).

FIG. 8 depicts an immunoblot showing expression of full length mature hIFNγ (arrow) by BCG Tice pNBV1-P23.5-plcB-SP(+3)-co-hIFNγ-v2 (rBCG-plcB-hIFNγ). Bands are also observed for hIFNγ without the signal peptide cleaved off (marked with an asterisk) as well as several breakdown products that run lower than the mature hIFNγ. Std, commercial recombinant hIFNγ.

FIG. 9 depicts an immunoblot showing no expression of full length mature hIFNγ (arrow) by BCG Tice pNBV1-P23.5-torA-SP(+4)-co-hIFNγ-v2-c-myc (rBCG-torA-hIFNγ) or BCG Tice pNBV1-P23.5-phoD-SP(+6)-co-hIFNγ-v2 (rBCG-phoD-hIFNγ). Four individual clones for each strain were analyzed.

FIG. 10 depicts an immunoblot showing expression of hIFNγ by *M. smegmatis* strains with the following plasmids: (1) pNBV1-P23.5-phoD-SP(+6)-co-hIFNγ-v2, (2) pNBV1-P23.5-plcB-SP(+3)-co-hIFNγ-v2, (3) pNBV1-P23.5-phoD-SP(+6)-co-hIFNγ-v2-c-myc, (4) pNBV1-P23.5-plcB-SP(+3)-co-hIFNγ-v2-c-myc, and (5) pNBV1-P23.5-torA-SP(+4)-co-hIFNγ-v2-c-myc. Strains 3, 4, and 5 expressed hIFNγ with a C-terminal c-myc epitope tag. The arrow (left) denotes full length mature hIFNγ and the arrowhead (right) denotes full length mature hIFNγ with the c-myc tag. The bands marked by an asterisk are hIFNγ without the signal peptide cleaved off.

FIG. 11 depicts an immunoblot showing stable expression of full length mature hIFNγ (arrow) by BCG Tice pNBV1-P23.5-Met-co-hIFNγ-v2 (rBCG-Met-hIFNγ) and BCG Tice pNBV1-P23.5-plcB-SP(+3)-co-hIFNγ-v2 (rBCG-plcBhIFNγ) after four subcultures (~40 generations) in the presence (+hyg) or absence (−hyg) of hygromycin. Bands are also observed for hIFNγ without the signal peptide cleaved off (marked with an asterisk, rBCG-plcB-hIFNγ) as well as several breakdown products that run lower than the mature hIFNγ (both strains). The mature hIFNγ produced by rBCG-plcB-hIFNγ is a minor band and the amount produced is much less than that produced by rBCG-Met-hIFNγ, a vaccine construct that lacks a signal peptide.

Figure 12:
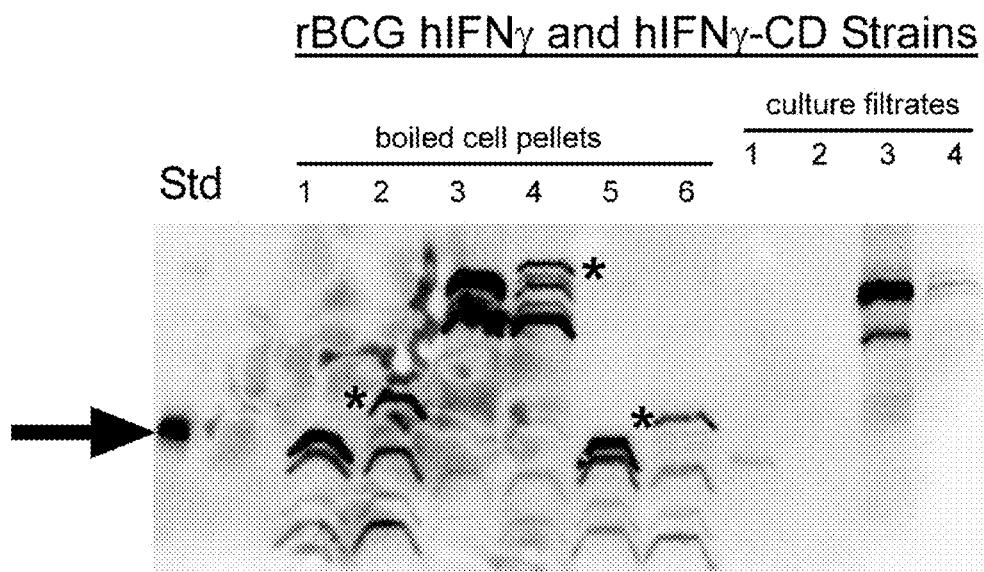

FIG. 12 depicts an immunoblot showing expression of hIFNγ and hIFNγ-CD (covalent dimer) by BCG (1 through 4) and rBCG30-ARMF-II (5 and 6) strains with the following plasmids: pNBV1-P23.5-Met-co-hIFNγ-v2 (1 and 5), pNBV1-P23.5-plcB-SP(+3)-co-hIFNγ-v2 (2 and 6), pNBV1-P23.5-Met-co-hIFNγ-v2-CD (3), and pNBV1-P23.5-plcB-SP(+3)-co-hIFNγ-v2-CD (4). The arrow (left) denotes full length mature hIFNγ and the arrowhead (right) denotes full length mature hIFNγ-CD. The mature hIFNγ and hIFNγ-CD produced using the PlcB signal peptide (2, 4, and 6) is a minor band and the amount produced is much less than that produced by the strains that lack a signal peptide (1, 3, and 5). The bands marked by an asterisk are hIFNγ without the signal peptide cleaved off.

Figures 13, 14:
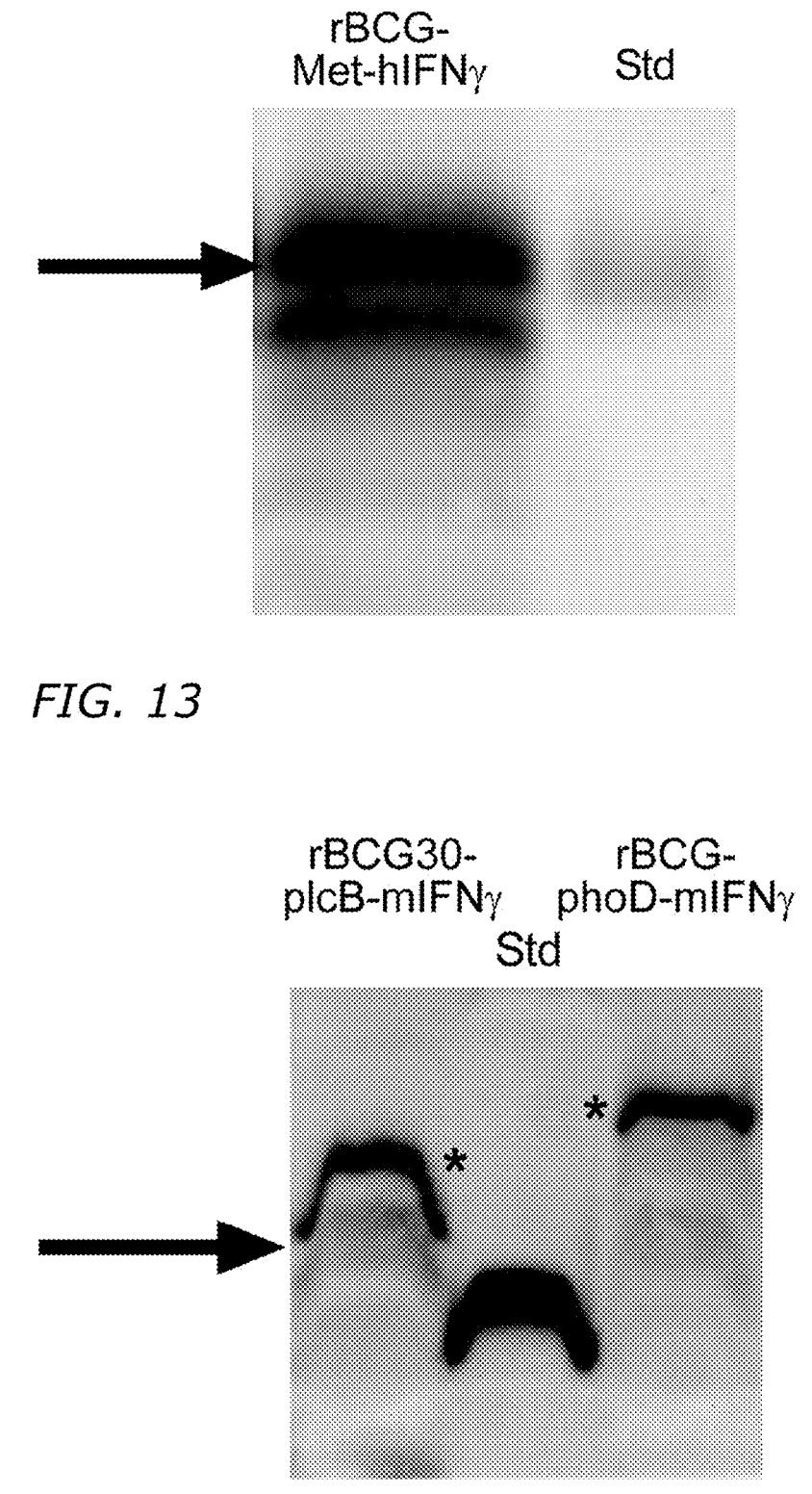

FIG. 13 depicts an immunoblot showing expression of full length mature hIFNγ (arrow) by BCG Tice pNBV1-P23.5-Met-co-hIFNγ-v2 (rBCG-Met-hIFNγ). A minor band is also observed for a breakdown product that runs lower than the mature hIFNγ.

FIG. 14 depicts an immunoblot showing expression of mIFNγ by rBCG30-ARMF-II Tice pNBV1-P23.5-plcB-SP(+3)-Met-co-mIFNγ (rBCG30-plcB-mIFNγ) and BCG Tice pNBV1-P23.5-phoD-SP(+6)-Met-co-mIFNγ (rBCG-phoD-mIFNγ). Only a small portion of the total expressed mIFNγ is present as the full length mature mIFNγ (arrow). The major bands are mIFNγ without the signal peptides cleaved off (marked with an asterisk). Recombinant mIFNγ is susceptible to cleavage and often runs faster than the predicted molecular weight on SDS-PAGE gels, as was observed here.

Figure 15:
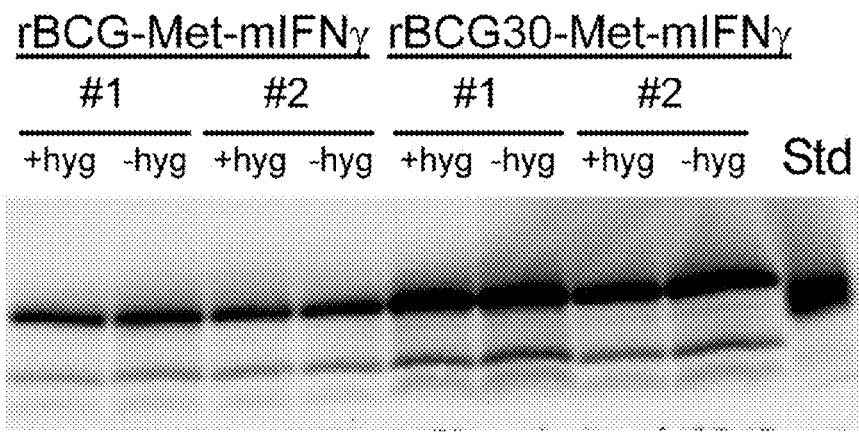

FIG. 15 depicts an immunoblot showing stable expression of full length mature mIFNγ (arrow) by BCG Tice pNBV1-P23.5-Met-co-hIFNγ-v2 (rBCG-Met-mIFNγ) and rBCG30-ARMF-II Tice pRE1-Prrs(short)-Met-co-mIFNγ (rBCG30-Met-mIFNγ) after two subcultures (~20 generations) in the presence (+hyg) or absence (−hyg) of hygromycin (#1, first subculture; #2, second subculture).

Figure 16:
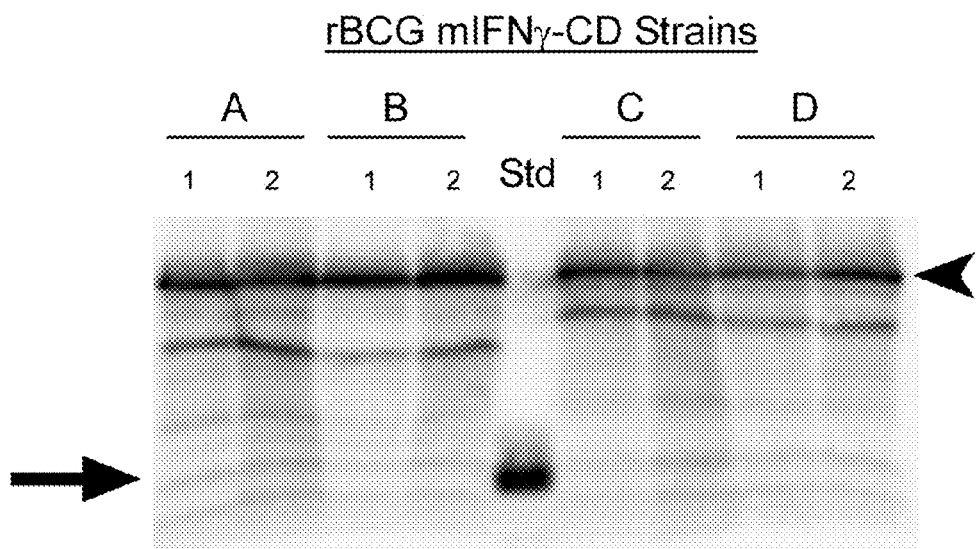

FIG. 16 depicts an immunoblot showing expression of full length mature mIFNγ-CD and mIFNγ-CD-ML (arrowhead) by the following strains (2 clones per strain were analyzed): A, BCG Tice pRE1-Prrs(short)-Met-co-mIFNγ-CD-ML; B, rBCG30-ARMF-II Tice pRE1-Prrs(short)-Met-co-mIFNγ-CD-ML; C, BCG Tice pRE1-Prrs(short)-Met-co-mIFNγ-CD; D, rBCG30-ARMF-II Tice pRE1-Prrs(short)-Met-co-mIFNγ-CD.

Figure 17:
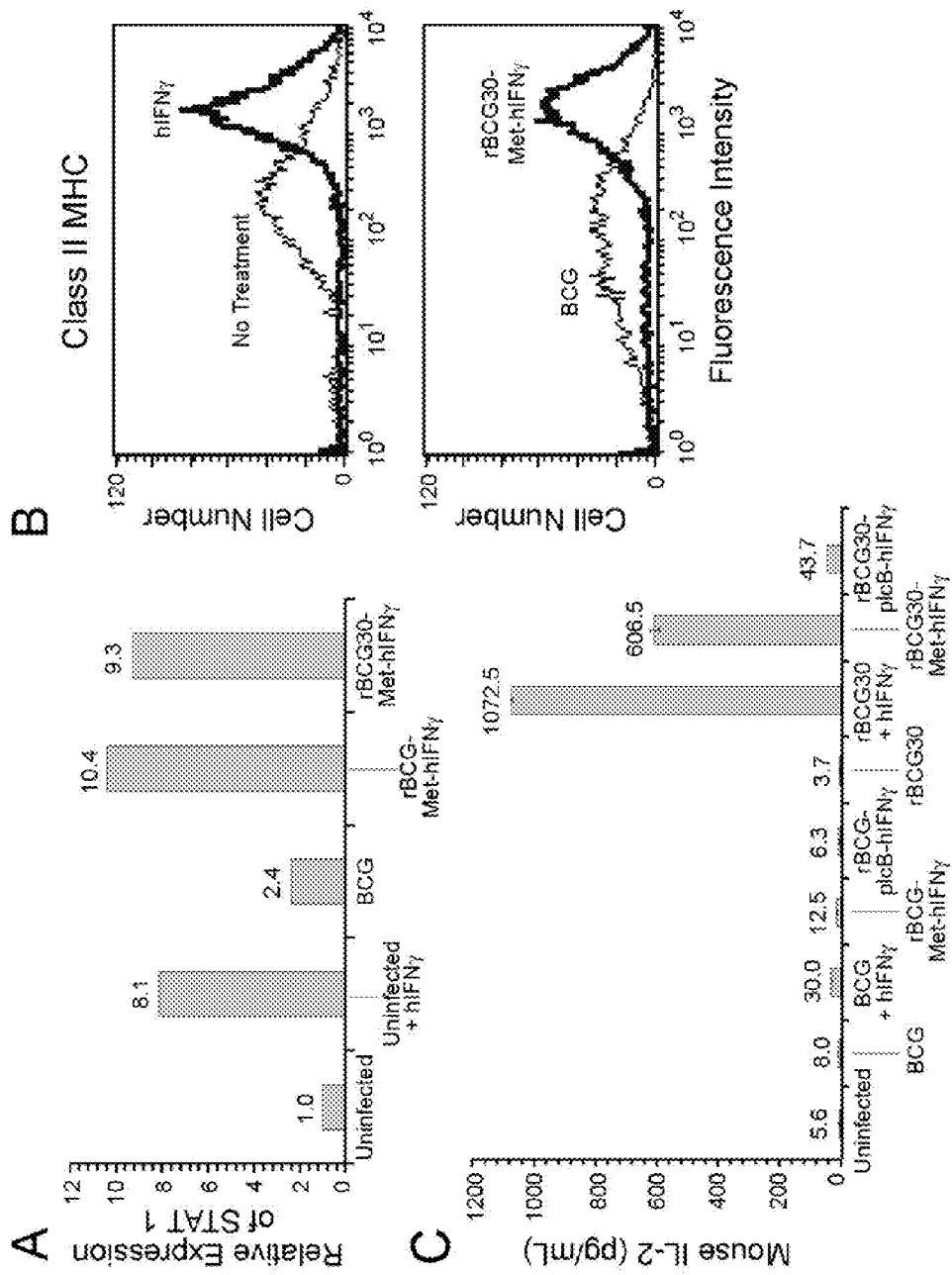

FIG. 17 depicts recombinant BCG vaccines expressing human IFNγ advantageously immunomodulating human macrophages in co-culture. FIG. 17A depicts induction of STAT1 mRNA, an important IFNγ-activated transcription factor, in human THP-1 macrophages, by BCG Tice pNBV1-P23.5-Met-co-hIFNγ-v2 (rBCG-Met-hIFNγ) and rBCG30-ARMF-II Tice pNBV1-P23.5-Met-co-hIFNγ-v2 (rBCG30-Met-hIFNγ). FIG. 17B depicts upregulation of MHC class II molecules on the surface of human monocytes (CD14+) by rBCG30-Met-hIFNγ compared with BCG (Lower Panel), similar to the effect of pure recombinant hIFNγ on the monocytes (Upper Panel). FIG. 17C depicts dramatically enhanced presentation of an immunodominant 30 kDa antigen epitope on class II MHC molecules in human THP-1 macrophages induced by rBCG30-Met-hIFNγ, as assessed by IL-2 production by a T-cell hybridoma cell line specific for this MHC class II-epitope complex; the increase is comparable to adding purified hIFNγ to rBCG30-ARMF-II Tice (rBCG30). The quantum increase in antigen presentation induced by the bimodal rBCG30-Met-hIFNγ is dependent upon its co-expression of the 30 kDa antigen and hIFNγ since unimodal vaccines expressing only one of these two proteins show little or no increase.

FIG. 18 depicts recombinant BCG vaccines expressing mouse IFNγ advantageously immunomodulate mouse macrophages in co-culture. FIG. 18A depicts induction of STAT1 mRNA by BCG Tice pRE1-Prrs(short)-Met-co-mIFNγ (rBCG-Met-mIFNγ) and rBCG30-ARMF-II Tice pRE1-Prrs (short)-Met-co-mIFNγ (rBCG30-Met-mIFNγ) in mouse RAW 264.7 macrophages. FIG. 18B depicts that bimodal vaccines expressing mIFNγ and the *M. tuberculosis* 30-kDa major secretory protein, rBCG30-Met-mIFNγ and rBCG30p-Met-co-mIFNγ Tice pRE13.2 (rBCG30p-Met-mIFNγ), show enhanced presentation of an immunodominant 30 kDa antigen epitope on class II MHC molecules in mouse bone marrow derived macrophages, as assessed by IL-2 production by a T-cell hybridoma cell line specific for this MHC class II-epitope complex; the increase is comparable to adding purified mIFNγ to rBCG30-ARMF-II Tice (rBCG30). The enhanced antigen presentation induced by the bimodal vaccines is dependent upon their co-expression of the 30 kDa antigen and mIFNγ since unimodal vaccines expressing only one of these two proteins show little increase.

DEFINITION OF TERMS

To facilitate an understanding of the following Detailed Description, Examples and appended claims it may be useful to refer to the following definitions. These definitions are non-limiting in nature and are supplied merely as a convenience to the reader.

Attenuated: As used herein, "attenuated" refers to microorganisms that are weakened and less virulent and are capable of stimulating an immune response and creating immunity but not causing illness.

Auxotroph or auxotrophic: As used herein "auxotroph" refers to a microorganism having a specific nutritional requirement not required by the wild-type organism. In the absence of the required nutrient the auxotroph will not grow whereas the wild-type will thrive.

Bimodal: As used herein a "bimodal" vaccine refers to a rBCG vaccine expressing both a *M. tuberculosis* protein and a cytokine.

Gene: A "gene" as used herein refers to at least a portion of a genetic construct having a coding region for a protein and a promoter and/or other regulatory sequences required for, or that modify the expression of, the genetic construct.

Genetic Construct: A "genetic construct" as used herein shall mean a nucleic acid sequence encoding for at least one major extracellular protein from at least one intracellular pathogen. In one embodiment of the present invention the genetic construct is extrachromosomal DNA.

Growth Regulatable: As used herein the term "growth regulatable" refers to an auxotrophic or metabolically impaired form of the present invention's immunogenic compositions. Growth is regulated by providing a nutrient essential for the auxotroph's growth at a concentration sufficient to induce growth.

Host: As used herein "host" refers to the recipient of the present immunogenic compositions. Exemplary hosts are mammals including, but not limited to, primates, rodents, cows, horses, dogs, cats, sheep, goats, pigs and elephants. In one embodiment of the present invention the host is a human. For the purposes of this disclosure host is synonymous with "vaccinee."

Immunogen: As used herein the term "immunogen" shall mean any substrate that elicits an immune response in a host. Immunogens of the present invention include, but are not limited to major extracellular proteins, and their recombinant forms, derived from intracellular pathogens, such as, but not limited members of the genus *Mycobacterium*.

Immunogenic Composition: An "immunogenic composition" as used herein comprises a recombinant vector, with or without an adjuvant, such as an intracellular pathogen, that expresses and/or secretes an immunogen in vivo and wherein the immunogen elicits an immune response in the host. The immunogenic compositions disclosed herein may be prototrophic, auxotrophic or metabolically impaired transformants. The immunogenic compositions of the present invention may or may not be immunoprotective or therapeutic. When the immunogenic compositions of the present invention prevent, ameliorate, palliate or eliminate disease from the host then the immunogenic composition may optionally be referred to as a vaccine. However, the term immunogenic composition is not intended to be limited to vaccines.

Major extracellular protein: As used herein, the term "major extracellular protein" refers to a protein exported or otherwise released abundantly into the supernatant fluid of *M. tuberculosis* growing in broth culture and is synonymous with "major secretory protein." The present inventors have previously described and characterized the mycobacterial major extracellular proteins of the present invention. The descriptions and characterization of the present major extracellular proteins can be found, without limitation, in U.S. Pat. No. 6,599,510, issued Jul. 29, 2003, the entire contents of which are hereby incorporated by reference.

Metabolically impaired: As used herein "metabolically impaired" shall mean a recombinant expression vector, specifically a recombinant Bacille Calmette Guérin (rBCG), that has an altered or deleted gene that is essential for normal metabolism. In the present case, the metabolic alteration results in a rBCG that cannot divide in vivo unless the nutrient is provided to the rBCG (pre-loading) prior to the rBCG being administered in vivo.

Nucleic Acid Sequence: As used herein the term "nucleic acid sequence" shall mean any continuous sequence of nucleic acids.

Prototrophic: As used herein "prototrophic" refers to a rBCG that does not require any substance in its nutrition additional to those required by the wild-type.

Transformant: As used herein a "transformant" refers to a microorganism that has been transformed with at least one heterologous or homologous nucleic acid molecule encoding a polypeptide that is expressed and/or secreted. In one embodiment of the present invention the transformant is BCG.

Unimodal: As used herein a "unimodal" vaccine refers to a rBCG vaccine expressing only a *M. tuberculosis* protein or a cytokine, but not both.

DETAILED DESCRIPTION OF THE INVENTION

The present invention provides methods for producing recombinant immunogenic compositions for preventing or treating diseases of intracellular pathogens in humans and animals, immunogenic compositions against diseases of intracellular pathogens in humans and animals, and a new approach to producing immunogenic compositions against tuberculosis, leprosy, other mycobacterial diseases, and other intracellular pathogens.

The invention is useful for preventing infection caused by *Mycobacterium tuberculosis*, the agent of tuberculosis, infection by other pathogenic strains of *Mycobacteria* in humans and/or animals including *Mycobacterium bovis*, *Mycobacterium avium intracellulare* and *Mycobacterium leprae*; and infection by intracellular pathogens in general.

A safe and effective immunogenic composition against *M. tuberculosis* that is more potent than the currently available vaccine is sorely needed. The only currently available vaccine, *Mycobacterium bovis* strain Bacille Calmette Guérin (BCG), is of variable efficacy. Studies have failed to demonstrate significant protection. The potency of BCG has been estimated to be approximately 50%. Hence, an immunogenic composition that improved the potency of BCG by even a small amount could have a tremendous impact on disease incidence.

The present inventors have previously disclosed recombinant BCG immunogenic compositions (rBCG30) expressing and secreting the *M. tuberculosis* 30 kDa major secretory (extracellular) protein (Horwitz et al. Proc. Natl. Acad. Sci. USA 97:13853-13858, 2000, incorporated by reference herein for all it discloses regarding rBCG immunogenic compositions). These immunogenic compositions were more potent than BCG in the highly relevant guinea pig model. One of the immunogenic compositions, rBCG30 Tice I (pSMT3-MTB30) is used in the studies described below.

Recombinant BCG Immunogenic Compositions Co-Expressing Host Immunostimulatory Cytokines and *M. tuberculosis* Major Extracellular Proteins Previously, it was known that the immunostimulatory cytokines interleukin 2 (IL-2), interleukin 12 (IL-12), granulocyte-macrophage colony stimulating factor (GM-CSF) and interferon gamma (INFγ) are associated with enhanced cell-mediated immunity against intracellular pathogens including *Mycobacterium tuberculosis*. For example, IL-12 enhances the resistance of mice to *M. tuberculosis* and mice lacking INFγ show increased susceptibility to *M. tuberculosis*. These immunostimulatory cytokines, when present in close proximity to the *M. tuberculosis* 30 kDa major secretory protein or other *M. tuberculosis* major extracellular proteins can enhance the protective immune response against tuberculosis induced by the extracellular proteins. Moreover, a recombinant BCG immunogenic composition co-expressing one of these immunostimulatory cytokines and the 30 kDa major secretory protein or other *M. tuberculosis* major extracellular proteins induces greater protective immunity than a recombinant BCG vaccine expressing the extracellular protein in the absence of the immunostimulatory protein.

Previous studies have shown that immunostimulatory cytokines, e.g. IL-2 and IL-12, can augment the efficiency of subunit vaccines (Baldwin et al. Infect. Immun. 66:2951-2959, 1998). However, none of the previously reported subunit vaccines have approached the efficacy of BCG.

Recombinant BCG expressing various murine and human cytokines have previously been reported (Murray et al. Proc. Natl. Acad. Sci. USA 93:934-939, 1996; O'Donnell et al. Infect. Immun. 62:2508-2514, 1994). However, such cytokine-producing recombinant BCG vaccines did not induce more potent protection in animal models than BCG alone. The present inventors have determined that a recombinant BCG vaccine expressing only INFγ was not more potent than the parent BCG strain. Surprisingly, the recombinant BCG co-expressing INFγ and the 30 kDa *M. tuberculosis* major secretory protein was more potent than rBCG30, the strain only expressing the 30 kDa protein. Thus, when expressed by BCG, INFγ did not enhance the level of protective immunity conferred by BCG alone, but when expressed by rBCG30, it did enhance the level of protective immunity conferred by rBCG30 alone. Therefore, the present inventors have determined that the co-expression of a majorly abundant extracellular antigen from an intracellular pathogen and a cytokine will result in enhanced protective immunity.

The present invention provides recombinant BCG immunogenic compositions expressing cytokines including, but not limited to, interleukin-2 (IL-2), interleukin-10 (IL-10), interleukin-12 (IL-12), interleukin-4 (IL-4), interleukin-6 (IL-6), interleukin-7 (IL-7), interleukin-8 (IL-8), interleukin-15 (IL-15), interleukin-17 (IL-17), interleukin-18 (IL-18), interferon gamma, tumor necrosis factor alpha (TNF-alpha), granulocyte macrophage colony stimulating factor (GM-CSF). The human cytokines IL-2, IL-12, and GM-CSF have been reported to be active in the guinea pig and active in non-glycosylated form. Additionally, rBCGs expressing cytokine receptors such as, but not limited to, the soluble IL-4 receptor (sIL4R) and the receptors for IL-2, IL-4, IL-7, IL-12, IFNs, GM-CSF or TNF-alpha are disclosed.

T lymphocytes are a major source of cytokines. These cells bear antigen specific receptors on their cell surface to allow recognition of foreign pathogens. They can also recognize normal tissue during episodes of autoimmune diseases. There are two main subsets of T lymphocytes, distinguished by the presence of cell surface molecules known as CD4 and CD8. T lymphocytes expressing CD4 are also known as helper T cells, and these are regarded as being the most prolific cytokine producers. This subset can be further subdivided into TH1 and TH2, and the cytokines they produce are known as TH1-type cytokines and TH2-type cytokines.

TH1-type cytokines tend to produce the proinflammatory responses responsible for killing intracellular parasites and for perpetuating autoimmune responses. Interferon gamma is the main TH1 cytokine. Excessive proinflammatory responses can lead to uncontrolled tissue damage, so there needs to be a mechanism to counteract this. The TH2-type cytokines include interleukins 4, 5, and 13, which are associated with the promotion of IgE and eosinophilic responses in atopy, and also interleukin-10, which has more of an anti-inflammatory response. In excess, TH2 responses will counteract the TH1 mediated microbicidal action. The optimal scenario would therefore seem to be that humans should produce a well balanced TH1 and TH2 response, suited to the immune challenge.

Many researchers regard allergy as a TH2 weighted imbalance, and recently immunologists have been investigating ways to redirect allergic TH2 responses in favor of TH1 responses to try to reduce the incidence of atopy. Some groups have been looking at using high dose exposure to allergen to drive up the TH1 response in established disease, and other groups have been studying the use of mycobacterial vaccines in an attempt to drive a stronger TH1 response in early life.

While a TH1 type of immune response is thought to promote immunoprotection against intracellular pathogens including M. tuberculosis, a TH2 type of immune response may be counterproductive. A shift towards a TH2 type response and cytokine profile has been found in tuberculosis patients. Based on the evidence that the soluble (extracellular) portion of the human interleukin 4 receptor can bind to interleukin 4 (IL-4) and the description of its molecular structure, a recombinant immunogenic composition expressing and secreting this soluble receptor fragment could competitively bind to circulating IL-4, significantly downmodulating the TH2 response to vaccine antigens, and shift the TH1 to TH2 ratio in favor of a TH1 response. Accordingly, to suppress a potential TH2 response to the antigens expressed by the immunogenic compositions of the present invention, a recombinant BCG expressing the IL-4 antagonist—soluble IL-4 Receptor (sIL4R) was produced.

The present invention encompasses several types of immunogenic compositions. One group of immunogenic compositions consists of recombinant strains of BCG Tice expressing and secreting various human or animal immunostimulatory molecules, host molecules that direct the immune response toward a TH1 type of immune response, or host molecules that direct the immune response away from a TH2 type of immune response. A second group of immunogenic compositions consists of recombinant strains of BCG Tice that express and secrete various human or animal immunostimulatory molecules, host molecules that direct the immune response toward a TH1 type of immune response, or host molecules that direct the immune response away from a TH2 type of immune response, and express a pathogen's major extracellular protein. Each immunogenic composition is administered intradermally or by another route, e.g. subcutaneously, intranasally, inhaled, or even orally to a mammalian host. The immunogenic compositions induce a strong cell-mediated immune response to pathogen antigens in the immunogenic composition. The immunogenic composition subsequently protects the mammalian hosts against infection with *M. tuberculosis, Mycobacterium leprae, Mycobacterium avium, Mycobacterium avium intracellulare*, other *Mycobacteria*, and other intracellular pathogens.

The current commercially available vaccine against tuberculosis is of limited efficacy against pulmonary tuberculosis. The immunogenic compositions of the present invention are more potent than the current commercially available vaccine in protecting against pulmonary tuberculosis and dissemination of bacteria to the spleen and other organs.

In one embodiment, the immunogenic compositions use extrachromosomal nucleic acids to express at least one recombinant immunogenic antigen or cytokine gene and placing this gene(s) under the control of a strong promoter, preferably protein-specific promoter sequences. In another embodiment, the immunogenic composition comprises recombinant organisms expressing at least one recombinant immunogenic antigen or cytokine gene from nucleic acid sequences integrated into the immunogenic composition's genomic DNA. In certain embodiments, an antigen gene is integrated into the immunogenic composition's genome and the cytokine gene is expressed from a plasmid. In other embodiments both the antigen and the cytokine are expressed from a plasmid. In one embodiment, the promoter is not a heat shock promoter or a stress protein promoter. As a result, intracellular pathogen immunogenic compositions having surprisingly superior specificity and potency than existing subunit or attenuated intracellular pathogen immunogenic compositions are provided.

Promoters useful for regulating the expression of genes in the immunogenic compositions of the present invention include a variety of promoters well known to persons or ordinary skill in the art. Particularly useful are strong promoters. The term "strong promoter" refers to a promoter that allows expression of the protein at a level at least as great as the level of the endogenous protein and preferably several times greater. Non-limiting examples of suitable strong promoters include, the promoter for rrs (also known as rrnS, MTB000019 and the 16S ribosomal RNA gene) both in full-length and shortened forms; the promoter for fbpB, the 30 kDa mycolyl transferase; the promoter for glnA1, the glutamine synthetase GlnA1 protein; the promoter for pknH, also known as Rv1266c; the promoter for the 23.5 kDa protein mpt64 or Rv1980; and the promoter for heat shock protein 60 also known as groEL2. These promoters can be used to regulate expression of extrachromosomal nucleic acid sequences or nucleic acid sequences integrated into the recombinant organism's genome. In one embodiment, the promoter is not a heat shock promoter or a stress protein promoter. In yet other embodiments, signal sequences are included.

The technology described herein for enhancing the immune response of the host is applicable to other vaccines against intracellular pathogens such as vaccines or immunogenic compositions against pathogens including, but not limited to, *Francisella tularensis, Chlamydia* species, *Listeria monocytogenes, Brucella* species, *Yersinia pestis, Bacillus anthracis, Salmonella typhi, Leishmania* species, *Mycobacteria* species, *Trypanosoma cruzi, Toxoplasma gondii, Histoplasma capsulatum, Riskettsia* species, *Coxiella burnetii, Plasmodia* species that cause malaria, and viruses, including, but not limited to, Human Immunodeficiency Virus (HIV).

Furthermore, the recombinant immunogenic antigens over-expressed by the immunogenic compositions disclosed herein can be from species including, but not limited to, *Mycobacterium bovis, M. tuberculosis, M. leprae, M. kansasii, M. avium, Mycobacterium* sp., *Legionella pneumophila, L. longbeachae, L. bozemanii, Legionella* sp., *Rickettsia rickettsii, Rickettsia typhi, Rickettsia* sp., *Ehrlichia chaffeensis, Ehrlichia phagocytophila geno* group, *Ehrlichia* sp., *Coxiella burnetii, Leishmania* sp, *Toxpolasma gondii, Trypanosoma cruzi, Chlamydia pneumoniae, Chlamydia* sp, *Listeria monocytogenes, Listeria* sp, *Francisella tularensis, Bacillus anthracis*, and *Histoplasma* sp.

Furthermore, the recombinant immunogenic composition can comprise a virus vector selected from the group consisting of adenovirus, vaccinia, avipox, adeno-associated virus, modified Vaccinia Strain Ankara, Semliki Forest virus, poxvirus, and herpes viruses.

Suitable recombinant immunogenic antigens include the major extracellular proteins of *Mycobacteria* species including, but not limited to, the 12 kDa protein, 14 kDa protein, 16 kDa protein, 23 kDa protein, 23.5 kDa protein, 30 kDa protein, 32A kDa protein, 32B kDa protein, 45 kDa protein, 58 kDa protein, 71 kDa protein, 80 kDa protein, and 110 kDa protein and combinations thereof.

Recombinant BCG Containing Single and Double Plasmid Constructs Expressing Various Cytokines or their Receptors Recombinant BCG immunogenic compositions were constructed which express human INFγ as their only recombinant protein. Furthermore, rBCG expressing and secreting guinea pig INFγ was produced, to allow proof of principle testing in guinea pigs. Additionally, a recombinant BCG expressing bovine INFγ was constructed for use in a tuberculosis vaccine for cattle.

BCG immunogenic compositions 1, 2, and 3, described below, were generated by electroporating recombinant pNBV1 (Howard et al., Gene 166:181-182, 1995; Harth et al. Microbiol. 150:2143-2151, 2004, all of which are incorporated by reference herein for all they disclose regarding plasmids and methods for constructing recombinant compositions) constructs (cassettes containing promoter, leader, and coding regions were always inserted into the plasmid's multicloning site) into BCG Tice wild-type, while immunogenic compositions 4 through 9 (described below) were generated by electroporating recombinant pGB9.2 (Bachrach et al. Microbiol. 146:297-303, 2000, which is incorporated by reference herein for all it discloses regarding plasmids and methods for constructing recombinant compositions) constructs (cassettes containing promoter, leader, and coding regions were always inserted into the plasmid's multi-cloning site) into rBCG30 Tice (Horwitz et al., 2000). Single plasmid-containing recombinant clones were selected on 7H11 agar and in 7H9 liquid culture containing 50 μg/mL hygromycin, while double plasmid recombinant clones were selected likewise except that all media also contained 20 μg/mL kanamycin. All clones were screened for expression and, where applicable, secretion of their corresponding cytokine; the double plasmid containing clones were also screened for the secretion of recombinant *M. tuberculosis* 30 kDa major secretory protein. For the analyses of protein expression, culture filtrates were analyzed by reaction with protein specific antibodies on nitrocellulose membranes. Immunoblots were scanned and digitized to measure the amount of cytokine and 30 kDa major secretory protein each recombinant vaccine expresses.

1. Construct Expressing Human Interferon Gamma Intracellularly rBCG PhspX-hINFγ Tice: This immunogenic composition contains a recombinant pNBV1 plasmid expressing the mature human cytokine from the promoter of the hspX gene (Rv2031c; Rv numbers based on *M. tuberculosis* H37Rv genome sequence) of *M. tuberculosis*. Since the cloned gene only contains the coding region of the mature protein (cDNA containing plasmid obtained from ATCC, Manassas, Va.), expression of INFγ is limited to the intracellular milieu and occurs during late log phase when this promoter is induced (FIG. 1; immunoblot with specific polyvalent antibodies).

2. Construct Expressing and Secreting Human Interferon Gamma rBCG PLmpt64-hINFγ Tice: This immunogenic composition contains a recombinant pNBV1 plasmid expressing the mature human cytokine from the promoter (P) of the 23.5 kDa protein gene (mpt64 or Rv1980c) of *M. tuberculosis*. The presence of the 23.5 kDa protein's leader sequence (L) allows for the constitutive secretion of mature INFγ (FIG. 1).

Figure 2:
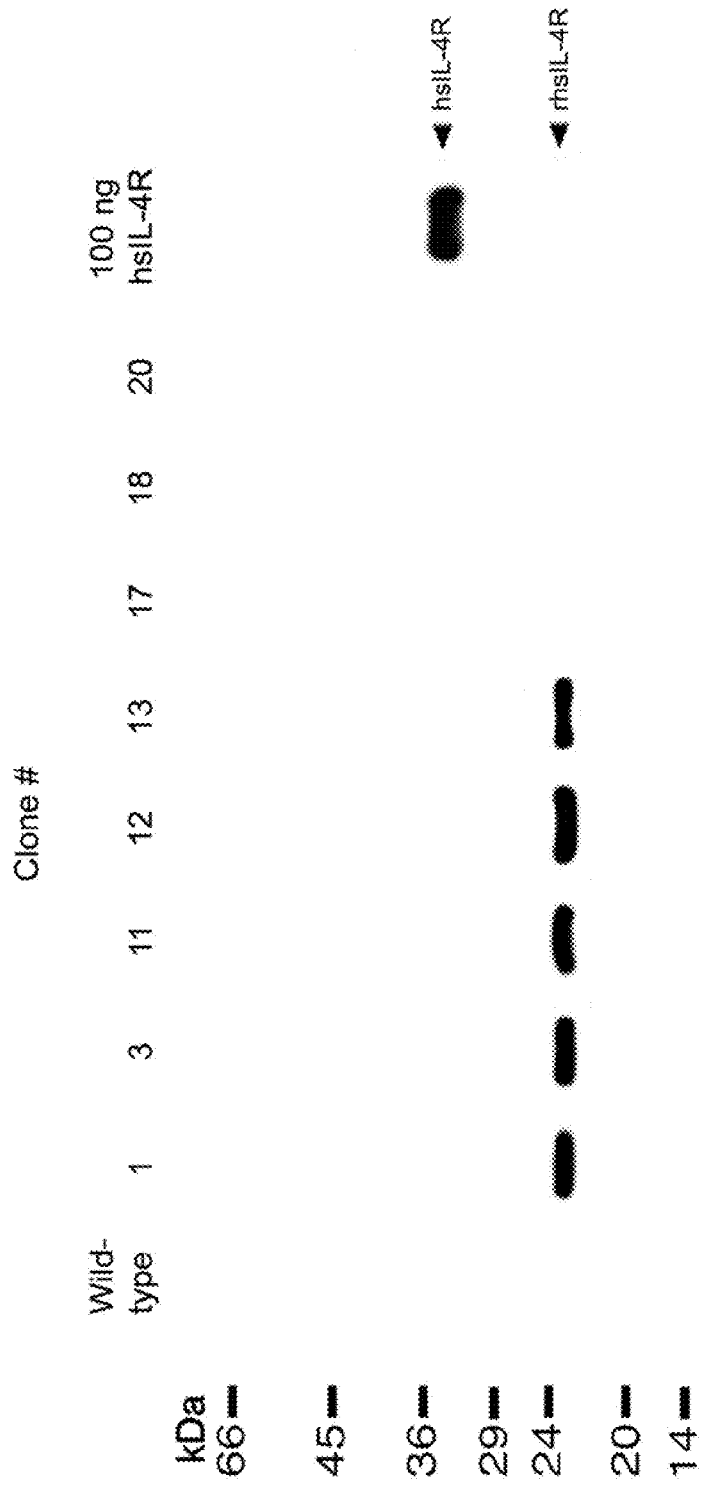

3. Construct Expressing and Secreting the Human Soluble Interleukin 4 Receptor Fragment (hsIL-4R)

rBCG PLmpt64-hsIL-4R Tice: This immunogenic composition contains a recombinant pNBV1 plasmid expressing the human soluble interleukin 4 receptor fragment (synthetic DNA fragment, GenScript Corp., Piscataway, N.J.) from the promoter of the 23.5 kDa protein gene (mpt64 or Rv1980c) of *M. tuberculosis*. The presence of the 23.5 kDa protein's leader sequence allows for the constitutive secretion of unglycosylated receptor fragment (the receptor fragment contains several potential N glycosylation sites which are utilized in eukaryotic cells, leading to receptor fragments of varying sizes which are approximately 10 kDa larger than the unglycosylated fragment). Several of the analyzed recombinant BCG clones were positive (FIG. 2; immunoblot with specific antibodies).

Figure 3:
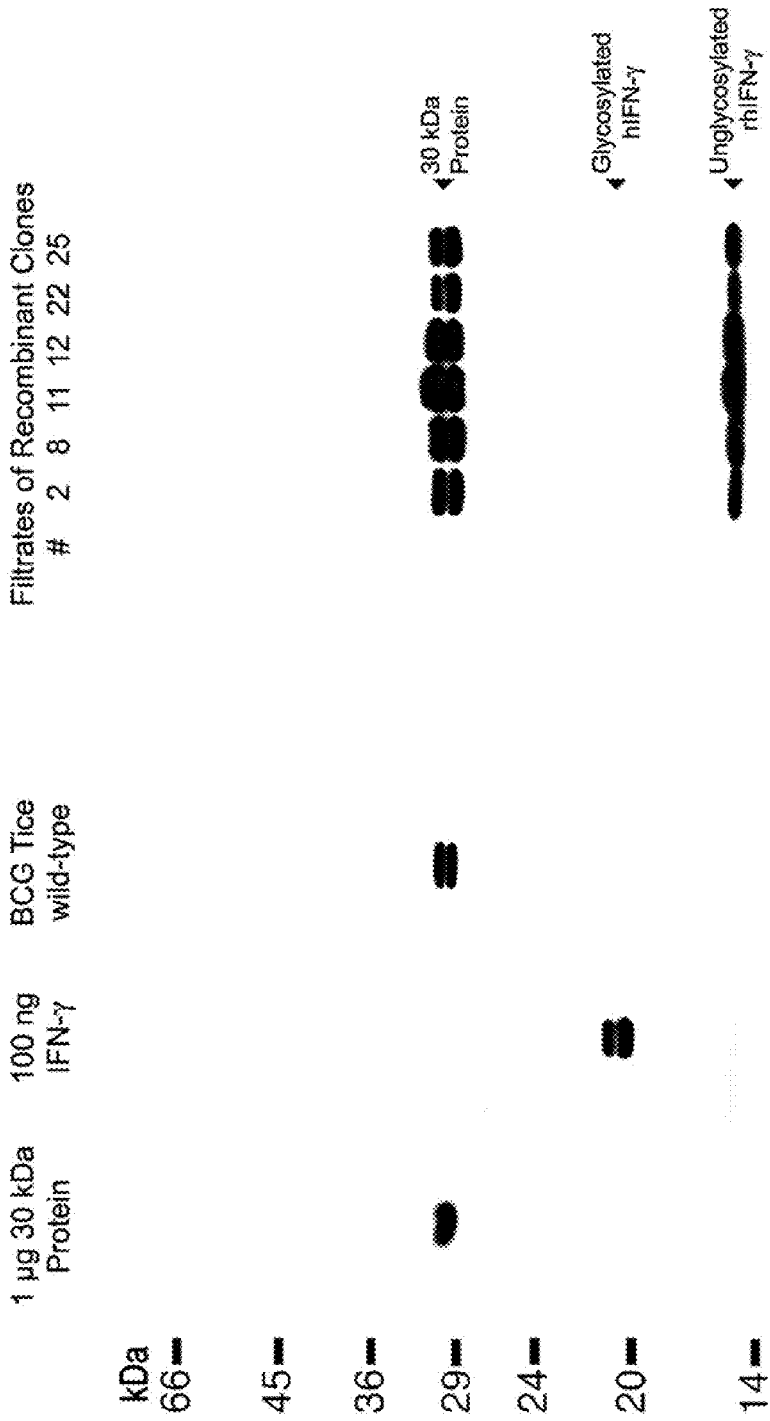

4. Construct Expressing and Secreting the *M. tuberculosis* 30 kDa Major Secretory Protein on One Plasmid and Human Interferon Gamma (hIFNγ) on a Second Plasmid rBCG30/hINFγ (pSMT3-MTB30; pGB9.2-hINFγ) Tice: This immunogenic composition is based on the rBCG30 Tice strain (Horwitz et al., 2000) which was modified by the introduction of a second compatible, recombinant plasmid pGB9.2. The recombinant pGB9.2, containing the coding region of the mature hIFNγ downstream of the promoter and leader peptide sequences of the *M. tuberculosis* 23.5 kDa protein gene (mpt64; Rv1980c) to allow expression and secretion of IFNγ, was electroporated into rBCG30 Tice bacteria to obtain a recombinant strain which secretes the 30 kDa major secretory protein from pSMT3 (Herrmann et al., EMBO J. 15:3547-3554, 1996; Anderson et al., J. Mol. Biol. 307:671-681, 2001, both of which are incorporated by reference herein for all they disclose regarding plasmids and methods for constructing recombinant compositions) and hIFNγ from pGB9.2. Several recombinant clones were obtained and analyzed by immunoblots. The expression pattern of the clones is shown in FIG. 3.

5. Construct Expressing and Secreting the *M. tuberculosis* 30 kDa Major Secretory Protein on One Plasmid and Guinea Pig IFNγ on a Second Plasmid rBCG30/gpINFγ (pSMT3-MTB30; pGB9.2-gpINFγ) Tice: This immunogenic composition is based on the rBCG30 Tice strain which was modified by the introduction of a second compatible, recombinant plasmid pGB9.2. The recombinant pGB9.2, containing the coding region of the mature guinea pig IFNγ downstream of the promoter and leader peptide sequences of the *M. tuberculosis* 23.5 kDa protein gene (mpt64; Rv1980c) to allow expression and secretion of IFNγ, was electroporated into rBCG30 Tice bacteria to obtain a recombinant strain which secretes the 30 kDa major secretory protein from pSMT3 and guinea pig IFNγ from pGB9.2. Several recombinant clones were obtained and analyzed by immunoblots using anti-hIFNγ immunoglobulins which cross-react with guinea pig IFNγ. Human and guinea pig IFNγ share 66% identity and 88% similarity, including the most important domain for species specific receptor binding (Walter et al., Nature 376:230-235, 1995): amino acids 129-132, human=KRKR, guinea pig=KRRR. The expression pattern of the clones is shown in FIG. 5.

Figure 5:
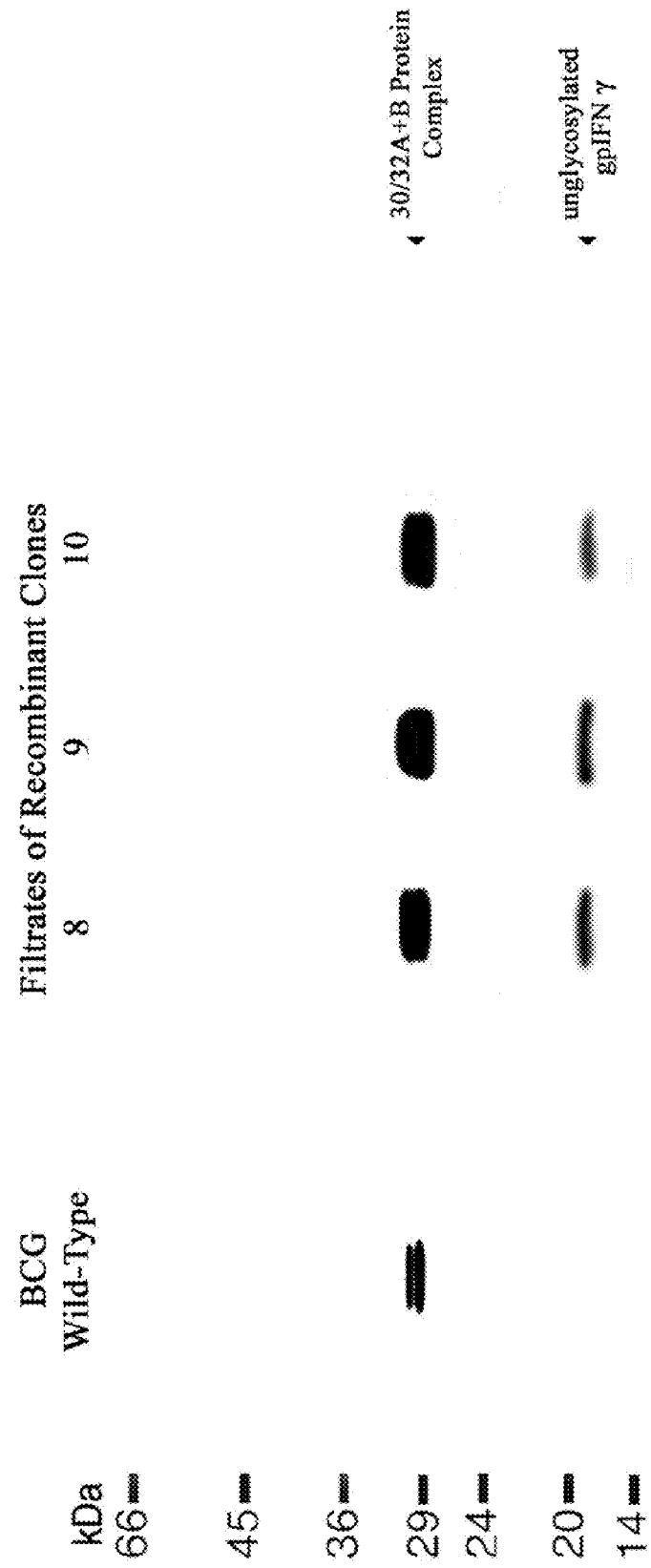

FIG. 5 depicts culture filtrates from rBCG Tice clones grown in medium containing 50 μg/mL hygromycin and 20 μg/mL kanamycin and probed for the expression and secretion of the *M. tuberculosis* 30 kDa protein and the mature guinea pig IFNγ by immunoblotting on a nitrocellulose membrane with protein specific antibodies. The antigen-antibody complexes were visualized by reaction with secondary antibodies coupled to horseradish peroxidase (HRPO), incubation with HRPO substrate, and exposure to X-ray film. The recombinant clones express the unglycosylated guinea pig IFNγ and, compared with the BCG wild-type control, over-express the *M. tuberculosis* 30 kDa protein.

6. Construct Expressing and Secreting the *M. tuberculosis* 30 kDa Major Secretory Protein on One Plasmid and Bovine IFNγ on a Second Plasmid rBCG30/bINFγ (pSMT3-MTB30; pGB9.2-bINFγ) Tice: This immunogenic composition is also based on the rBCG30 Tice strain. The recombinant plasmid pGB9.2, containing the coding region of the mature bovine IFNγ is introduced downstream of the promoter and leader peptide sequences of the *M. tuberculosis* 23.5 kDa protein gene (mpt64; Rv1980c) to allow expression and secretion of IFNγ, by electroporation into rBCG30 Tice bacteria to obtain a recombinant strain which secretes the 30 kDa major secretory protein from pSMT3 and bovine IFNγ from pGB9.2.

Figure 6:
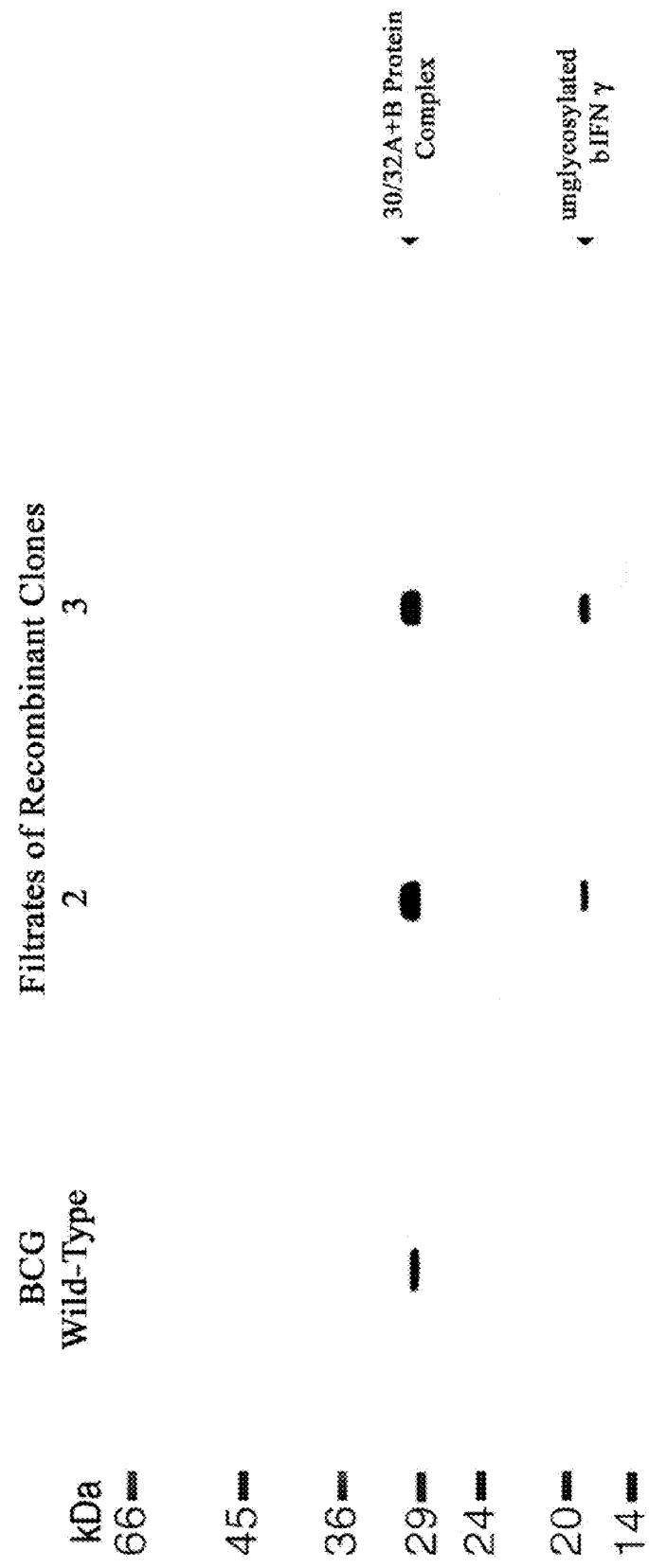

FIG. 6 depicts culture filtrates from rBCG Tice clones grown in medium containing 50 μg/mL hygromycin and 20 μg/mL kanamycin and probed for the expression and secretion of the *M. tuberculosis* 30 kDa protein and the mature bovine IFNγ by immunoblotting on a nitrocellulose membrane with protein specific antibodies. The antigen-antibody complexes were visualized by reaction with secondary antibodies coupled to HRPO, incubation with HRPO substrate, and exposure to X-ray film. The recombinant clones express the unglycosylated bovine IFNγ and, compared with the BCG wild-type control, over-express the *M. tuberculosis* 30 kDa protein.

Figure 4:
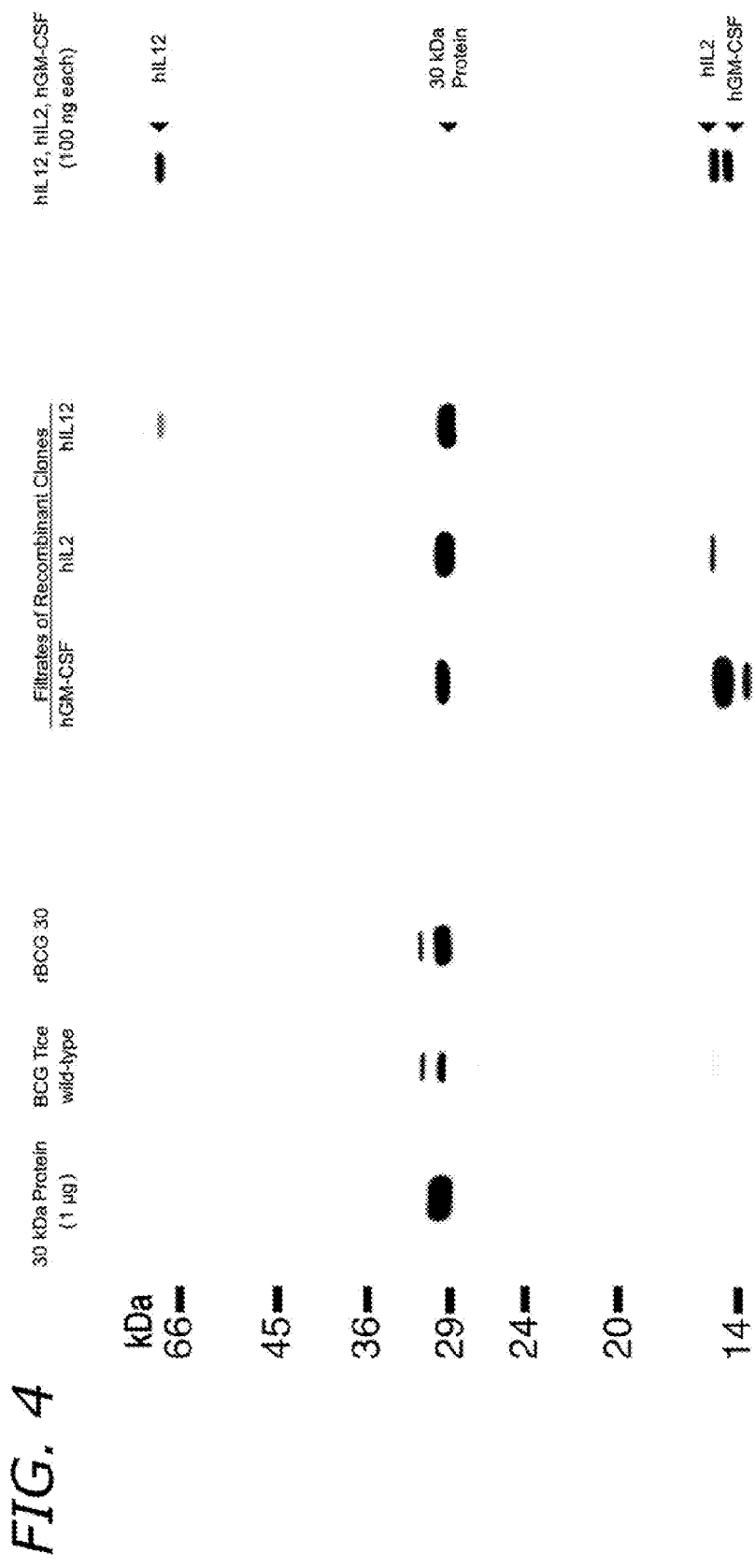

7. Construct Expressing and Secreting the *M. tuberculosis* 30 kDa Major Secretory Protein on One Plasmid and Human Granulocyte-Macrophage Colony Stimulating Factor (GM-CSF) on a Second Plasmid rBCG30/hGM-CSF(pSMT3-MTB30; pGB9.2-hGM-CSF) Tice: This vaccine is based on the rBCG30 Tice strain which was modified by the introduction of a second compatible, recombinant plasmid pGB9.2. The recombinant pGB9.2, containing the coding region of the mature human granulocyte-macrophage colony stimulating factor (cDNA clone obtained from ATCC) downstream of the promoter and leader peptide sequences of the *M. tuberculosis* 23.5 kDa protein gene (mpt64; Rv1980c) to allow expression and secretion of granulocyte-macrophage colony stimulating factor, was electroporated into rBCG30 Tice bacteria to obtain a recombinant strain which secretes the 30 kDa major secretory protein from pSMT3 and human granulocyte-macrophage colony stimulating factor from pGB9.2. Several recombinant clones were obtained and analyzed by immunoblots. The expression pattern of the clones is shown in FIG. 4.

8. Construct Expressing and Secreting the *M. tuberculosis* 30 kDa Major Secretory Protein on One Plasmid and Human Interleukin 2 (IL-2) on a Second Plasmid rBCG30/hIL-2 (pSMT3-MTB30; pGB9.2-hIL-2 Tice: This immunogenic composition is based on the rBCG30 Tice strain which was modified by the introduction of a second compatible, recombinant plasmid pGB9.2. The recombinant pGB9.2, containing the coding region of the mature human interleukin 2 downstream of the promoter and leader peptide sequences of the *M. tuberculosis* 23.5 kDa protein gene (mpt64; Rv1980c) to allow expression and secretion of interleukin 2, was electroporated into rBCG30 Tice bacteria to obtain a recombinant strain which secretes the 30 kDa protein from pSMT3 and human interleukin 2 from pGB9.2. Several recombinant clones were obtained and analyzed by immunoblots. The expression pattern of the clones is shown in FIG. 4.

9. Construct Expressing and Secreting the *M. tuberculosis* 30 kDa Major Secretory Protein on One Plasmid and Human Interleukin 12 (IL-12) on a Second Plasmid rBCG30/hIL-12 (pSMT3-MTB30; pGB9.2-hIL-12) Tice: This immunogenic composition is based on the rBCG30 Tice strain which was modified by the introduction of a second compatible, recombinant plasmid pGB9.2. The recombinant pGB9.2, containing the coding region of the mature human interleukin 12 downstream of the promoter and leader peptide sequences of the *M. tuberculosis* 23.5 kDa protein gene (mpt64; Rv1980c) to allow expression and secretion of interleukin 12, was electroporated into rBCG30 Tice bacteria to obtain a recombinant strain which secretes the 30 kDa major secretory protein from pSMT3 and human interleukin 12 from pGB9.2. Interleukin 12 is a heterodimer encoded on two separate genes whose gene products have to be assembled stoichiometrically to confer bioactivity to the protein complex. In recombinant form, it is frequently expressed as p70 by fusing the p35 to the carboxyl terminus of p40 and separating the two protein domains by an amino acid linker comprising a string of six glycines and one serine. Several recombinant clones were obtained and analyzed by immunoblots. The expression pattern of the clones is shown in FIG. 4.

10. Construct Expressing and Secreting the *M. tuberculosis* 30 kDa Major Secretory Protein on One Plasmid and Human Soluble Interleukin 4 Receptor on a Second Plasmid rBCG30/hsIL-4R (pSMT3-MTB30; pGB9.2-hsIL-4R) Tice: This immunogenic composition is based on the rBCG30 Tice strain which was modified by the introduction of a second compatible, recombinant plasmid pGB9.2. The recombinant pGB9.2, containing the coding region of the human soluble interleukin 4 receptor (soluble domain of the human IL-4 receptor) downstream of the promoter and leader peptide sequences of the *M. tuberculosis* 23.5 kDa protein gene (mpt64; Rv1980c) to allow expression and secretion of human soluble interleukin 4 receptor, was electroporated into rBCG30 Tice bacteria to obtain a recombinant strain which secretes the 30 kDa major secretory protein from pSMT3 and human soluble interleukin 4 receptor from pGB9.2. Several recombinant clones were obtained and analyzed by immunoblots. The expression pattern of two clones is shown in FIG. 7.

11. Additional Strains of rBCG Expressing Interferon Gamma

BCG Tice pNBV1-P23.5-Met-co-hIFNγ-v2. Construct expressing intracellular human interferon gamma (hIFNγ) from a plasmid (pNBV1), where the promoter was from the 23.5 kDa protein gene (mpt64 or Rv1980), and where the sequence for hIFNγ was codon-optimized for mycobacteria.

BCG Tice pNBV1-P23.5-plcB-SP(+3)-co-hIFNγ-v2. Construct expressing and secreting hIFNγ from a plasmid (pNBV1), where the promoter was from the 23.5 kDa protein gene (mpt64 or Rv1980), the sequence for hIFNγ was codon-optimized for mycobacteria, and the PlcB Tat signal peptide was used for secretion.

BCG Tice pNBV1-P23.5-torA-SP(+4)-co-hIFNγ-v2-c-myc. Construct designed to express and secrete hIFNγ from a plasmid (pNBV1), where the promoter was from the 23.5 kDa protein gene (mpt64 or Rv1980), the sequence for hIFNγ was codon-optimized for mycobacteria, the TorA Tat signal peptide was used for secretion, and a c-myc epitope tag was fused to the C-terminus. However, this construct only expressed truncated hIFNγ.

BCG Tice pNBV1-P23.5-phoD-SP(+6)-co-hIFNγ-v2. Construct designed to express and secrete hIFNγ from a plasmid (pNBV1), where the promoter was from the 23.5 kDa protein gene (mpt64 or Rv1980), the sequence for hIFNγ was codon-optimized for mycobacteria, and the PhoD Tat signal peptide was used for secretion. However, no clones were obtained that expressed hIFNγ.

BCG Tice pNBV1-P23.5-Met-co-hIFNγ-v2-CD. Construct expressing intracellular human IFNγ as a covalent dimer (hIFNγ-CD) from a plasmid (pNBV1), where the promoter was from the 23.5 kDa protein gene (mpt64 or Rv1980), and where the sequence for hIFNγ was codon-optimized for mycobacteria.

BCG Tice pNBV1-P23.5-plcB-SP(+3)-co-hIFNγ-v2-CD. Construct expressing and secreting human IFNγ as a covalent dimer (hIFNγ-CD) from a plasmid (pNBV1), where the promoter was from the 23.5 kDa protein gene (mpt64 or Rv1980), the sequence for hIFNγ was codon-optimized for mycobacteria, and the PlcB Tat signal peptide was used for secretion.

BCG Tice pNBV1-P23.5-torA-SP-co-hIFNγ-v2-CD. Construct expressing and secreting human IFNγ as a covalent dimer (hIFNγ-CD) from a plasmid (pNBV1), where the promoter was from the 23.5 kDa protein gene (mpt64 or Rv1980), the sequence for hIFNγ was codon-optimized for mycobacteria, and the TorA Tat signal peptide was used for secretion.

BCG Tice pRE1-Prrs(short)-Met-co-mIFNγ. Construct expressing intracellular mouse interferon gamma (mIFNγ) from a plasmid (pRE1), where the promoter was a shortened derivative of the rrs (rrnS or 16S ribosomal RNA gene) promoter lacking the boxA, boxB, and boxC elements, and where the sequence for mIFNγ was codon-optimized for mycobacteria.

BCG Tice pNBV1-P23.5-plcB-SP(+3)-Met-co-mIFNγ. Construct expressing and secreting mIFNγ from a plasmid (pNBV1), where the promoter was from the 23.5 kDa protein gene (mpt64 or Rv1980), the sequence for mIFNγ was codon-optimized for mycobacteria, and the PlcB Tat signal peptide was used for secretion.

BCG Tice pNBV1-P23.5-phoD-SP(+6)-Met-co-mIFNγ. Construct expressing and secreting mIFNγ from a plasmid (pNBV1), where the promoter was from the 23.5 kDa protein gene (mpt64 or Rv1980), the sequence for mIFNγ was codon-optimized for mycobacteria, and the PhoD Tat signal peptide was used for secretion.

BCG Tice pRE1-Prrs(short)-Met-co-mIFNγ-CD. Construct expressing intracellular mouse IFNγ as a covalent dimer (mIFNγ-CD) from a plasmid (pRE1), where the promoter was a shortened derivative of the rrs (rrnS or 16S ribosomal RNA gene) promoter lacking the boxA, boxB, and boxC elements, and where the sequence for mIFNγ was codon-optimized for mycobacteria.

BCG Tice pRE1-Prrs(short)-Met-co-mIFNγ-CD-ML. Construct expressing intracellular mouse IFNγ as a covalent dimer with a modified linker sequence (mIFNγ-CD-ML) from a plasmid (pRE1), where the promoter was a shortened derivative of the rrs (rrnS or 16S ribosomal RNA gene) promoter lacking the boxA, boxB, and boxC elements, and where the sequence for mIFNγ was codon-optimized for mycobacteria.

12. Recombinant rBCG30-ARMF-II Tice Expressing IFNγ rBCG30-ARMF-II Tice, formerly designated rBCG3011E, is a recombinant BCG expressing the *M. tuberculosis* 30 kDa major secretory protein (Antigen 85B) from the chromosome and is Antibiotic Resistance Marker Free.

rBCG30-ARMF-II Tice pNBV1-P23.5-Met-co-hIFNγ-v2. Construct expressing and secreting the *M. tuberculosis* 30 kDa major secretory protein from the chromosome and expressing intracellular human interferon gamma (hIFNγ) from a plasmid (pNBV1), where the promoter was from the 23.5 kDa protein gene (mpt64 or Rv1980), and where the sequence for hIFNγ was codon-optimized for mycobacteria.

rBCG30-ARMF-II Tice pNBV1-P23.5-plcB-SP(+3)-co-hIFNγ-v2. Construct expressing and secreting the *M. tuberculosis* 30 kDa major secretory protein from the chromosome and expressing and secreting hIFNγ from a plasmid (pNBV1), where the promoter was from the 23.5 kDa protein gene (mpt64 or Rv1980), the sequence for hIFNγ was codon-optimized for mycobacteria, and the PlcB Tat signal peptide was used for secretion.

rBCG30-ARMF-II Tice pNBV1-P23.5-phoD-SP(+6)-co-hIFNγ-v2. Construct expressing and secreting the *M. tuberculosis* 30 kDa major secretory protein from the chromosome and expressing and secreting hIFNγ from a plasmid (pNBV1), where the promoter was from the 23.5 kDa protein gene (mpt64 or Rv1980), the sequence for hIFNγ was codon-optimized for mycobacteria, and the PhoD Tat signal peptide was used for secretion.

rBCG30-ARMF-II Tice pNBV1-P23.5-torA-SP-co-hIFNγ-v2. Construct expressing and secreting the *M. tuberculosis* 30 kDa major secretory protein from the chromosome and expressing and secreting hIFNγ from a plasmid (pNBV1), where the promoter was from the 23.5 kDa protein gene (mpt64 or Rv1980), the sequence for hIFNγ was codon-optimized for mycobacteria, and the TorA Tat signal peptide was used for secretion.

rBCG30-ARMF-II Tice pNBV1-P23.5-Met-co-hIFNγ-v2-CD. Construct expressing and secreting the *M. tuberculosis* 30 kDa major secretory protein from the chromosome and expressing intracellular human IFNγ as a covalent dimer (hIFNγ-CD) from a plasmid (pNBV1), where the promoter was from the 23.5 kDa protein gene (mpt64 or Rv1980), and where the sequence for hIFNγ was codon-optimized for mycobacteria.

rBCG30-ARMF-II Tice pRE1-Prrs(short)-Met-co-mIFNγ. Construct expressing and secreting the *M. tuberculosis* 30 kDa major secretory protein from the chromosome and expressing intracellular mIFNγ from a plasmid (pRE1), where the promoter was a shortened derivative of the rrs (rrnS or 16S ribosomal RNA gene) promoter lacking the boxA, boxB, and boxC elements, and where the sequence for mIFNγ was codon-optimized for mycobacteria.

rBCG30-ARMF-II Tice pNBV1-P23.5-plcB-SP(+3)-Met-co-mIFNγ. Construct expressing and secreting the *M. tuberculosis* 30 kDa major secretory protein from the chromosome and expressing and secreting mIFNγ from a plasmid (pNBV1), where the promoter was from the 23.5 kDa protein gene (mpt64 or Rv1980), the sequence for mIFNγ was codon-optimized for mycobacteria, and the PlcB Tat signal peptide was used for secretion.

rBCG30-ARMF-II Tice pNBV1-P23.5-phoD-SP(+6)-Met-co-m IFNγ. Construct expressing and secreting the *M. tuberculosis* 30 kDa major secretory protein from the chromosome and expressing and secreting mIFNγ from a plasmid (pNBV1), where the promoter was from the 23.5 kDa protein gene (mpt64 or Rv1980), the sequence for mIFNγ was codon-optimized for mycobacteria, and the PhoD Tat signal peptide was used for secretion.

rBCG30-ARMF-II Tice pRE1-Prrs(short)-Met-co-mIFNγ-CD. Construct expressing and secreting the *M. tuberculosis* 30 kDa major secretory protein from the chromosome and expressing intracellular mouse IFNγ as a covalent dimer (mIFNγ-CD) from a plasmid (pRE1), where the promoter was a shortened derivative of the rrs (rrnS or 16S ribosomal RNA gene) promoter lacking the boxA, boxB, and boxC elements, and where the sequence for mIFNγ was codon-optimized for mycobacteria.

rBCG30-ARMF-II Tice pRE1-Prrs(short)-Met-co-mIFNγ-CD-ML. Construct expressing and secreting the *M. tuberculosis* 30 kDa major secretory protein from the chromosome and expressing intracellular mouse IFNγ as a covalent dimer with a modified linker sequence (mIFNγ-CD-ML) from a plasmid (pRE1), where the promoter was a shortened derivative of the rrs (rrnS or 16S ribosomal RNA gene) promoter lacking the boxA, boxB, and boxC elements, and where the sequence for mIFNγ was codon-optimized for mycobacteria.

13. Recombinant BCG Expressing the *M. tuberculosis* 30 kDa Major Secretory Protein and mIFNγ from a Plasmid rBCG30p-Met-co-mIFNγ Tice pRE13.2. Construct expressing intracellular mIFNγ and expressing and secreting the *M. tuberculosis* 30 kDa major secretory protein from a plasmid (pRE1), where the promoter driving expression of both genes was a shortened derivative of the rrs (rrnS or 16S ribosomal RNA gene) promoter lacking the boxA, boxB, and boxC elements, and where the sequence for mIFNγ was codon-optimized for mycobacteria.

Growth-Regulatable Immunogenic Compositions

The present invention provides recombinant BCG immunogenic compositions that a) are growth-limited and/or growth-regulatable and b) are growth-limited and/or growth-regulatable and secrete a *M. tuberculosis* major extracellular protein, in one non-limiting example, the *M. tuberculosis* 30 kDa major secretory protein.

Immunogenic compositions comprising a rBCG wherein the rBCG is metabolically impaired and wherein a siderophore and iron are used to regulate growth of the metabolically impaired strain are also provided. This rBCG has been rendered siderophore-dependent and iron-loadable. It can be grown in vitro in the presence of iron and a siderophore such as, but not limited to, mycobactin J or exochelin, and thereby loaded with iron. Subsequently, when administered to the host, it can use the stored iron to multiply for several generations. As some growth of a live vaccine in the host is necessary to induce a strong protective immune response, the capacity of the rBCG to divide several times in the host allows the generation of a strong protective immune response. At the same time, the limited capacity of the rBCG to multiply in the host, as a result of its inability to acquire iron in the host, renders it unable to cause disseminated disease in the immunocompromised host and therefore safer than BCG. The rBCG(mbtB)30 immunogenic composition, while safer than BCG because it can not disseminate in an immunocompromised host, is also more potent than BCG.

Additionally, growth regulatable recombinant BCG immunogenic compositions which can not grow more than a few generations in the host without a nutritional supplement are provided. These compositions are designed to be safer than BCG, because unlike BCG, such immunogenic composition can not disseminate in the host in the absence of the nutritional supplement. Growth-regulatable auxotrophic recombinant BCG immunogenic compositions are provided that are dependent upon small amounts of the vitamin pantothenate. The rBCG can be administered to the host without providing a nutrient supplement to the host, in which case it can only undergo a limited number of divisions using stored nutrient but a sufficient number of divisions to generate a potent protective immune response. Alternatively, the vaccine can be administered to the host and the host provided a large amount of the nutrient, which can be given safely and inexpensively to mammals in large quantities, facilitating its acquisition by the live recombinant immunogenic composition in the host. In one example, the nutrient is the vitamin pantothenate. Under such circumstances, the immunogenic composition can persist longer in the host and induce a stronger protective immune response. Should the vaccine begin to disseminate and cause illness the nutrient supplement can be readily terminated, thereby stopping growth of the organism in the host and preventing serious disease. The amount of pantothenate normally present in the host eating a normal diet is orders of magnitude less than that needed to provide sufficient pantothenate for the growth of the rBCG. One version of the novel live recombinant pantothenate-dependent BCG immunogenic composition over-expresses the *M. tuberculosis* 30 kDa major secretory protein.

Recombinant attenuated growth-regulatable immunogenic compositions are further disclosed in co-pending U.S. Provisional Patent Application No. 60/744,552 filed Apr. 10, 2006 and International Patent Application No. PCT/US2007/066348 filed on Apr. 10, 2007, the contents of both of which are incorporated herein in their entirety.

Example 1

Cell-Mediated, Humoral, and Protective Immunity Studies

Several studies of the efficacy of the immunogenic compositions of the present invention utilized guinea pigs because the guinea pig model is especially relevant to human tuberculosis clinically, immunologically, and pathologically. In contrast to the mouse and rat, but like the human, the guinea pig a) is susceptible to low doses of aerosolized *M. tubercu-* losis; b) exhibits strong cutaneous delayed-type hypersensitivity (DTH) to tuberculin; and c) displays Langhans giant cells and caseation in pulmonary lesions. However, whereas only about 10% of immunocompetent humans who are infected with *M. tuberculosis* develop active disease over their lifetime (half early after exposure and half after a period of latency), infected guinea pigs always develop early active disease. While guinea pigs differ from humans in this respect, the consistency with which they develop active disease after infection with *M. tuberculosis* is an advantage in trials of vaccine efficacy.

Aliquots were removed from logarithmically growing wild-type or recombinant BCG cultures and the bacteria were pelleted by centrifugation at 3,500×g for 15 min. The bacteria were then washed with 1× phosphate buffered saline (1×PBS, 50 mM sodium phosphate pH 7, 150 mM sodium chloride) and resuspended at a final concentration of $1\times10^4$ or $1\times10^7$ colony-forming units per ml in 1×PBS. The immunization inoculum contained $10^3$ or $10^6$ viable wild-type or recombinant BCG bacteria in a total volume of 100 μl.

Experiment 1

1. Immunization of Animals

Specific-pathogen free 250-300 g outbred male Hartley strain guinea pigs from Charles River Breeding Laboratories, in groups of 15 or 21, were sham-immunized by intradermal administration of buffer (15 animals total) or immunized intradermally with $10^3$ or $10^6$ CFU of one of the following strains of BCG (21 animals/group):

Group A: Sham-immunized (Sham)
Group B: $10^3$ BCGTice Parental Control (BCG)
Group C: $10^3$ rBCG30 Tice I (pSMT3-MTB30) (rBCG30)
Group D: $10^3$ rBCG30/hINFγ (pSMT3-MTB30; pGB9.2-hINFγ) Tice (rBCG30/hINFγ)
Group E: $10^6$ rBCG(mbtB) Tice grown in a low mycobactin J concentration (rBCG(mbtB) Lo Fe)
Group F: $10^6$ rBCG(mbtB) Tice grown in a high mycobactin J concentration (rBCG(mbtB) Hi Fe)
Group G: $10^6$ rBCG(mbtB)30 II (pNBV1-30) Tice grown in a low mycobactin J concentration (rBCG(mbtB)30 Lo Fe)
Group H: $10^6$ rBCG(mbtB)30 II (pNBV1-30) Tice grown in a high mycobactin J concentration (rBCG(mbtB)30 Hi Fe)

2. Cutaneous Delayed-type Hypersensitivity (DTH) to Purified Recombinant *M. tuberculosis* 30 kDa Major Secretory Protein (r30)

Ten weeks after immunization, 6 guinea pigs in each group were shaved over the back and injected intradermally with 10 μg of purified recombinant *M. tuberculosis* 30 kDa major secretory protein (r30) in 100 μl phosphate buffered saline. After 24 h, the diameter of erythema and induration was measured. A separate group of animals from the one used in the challenge studies was used for skin-testing to eliminate the possibility that the skin-test itself might influence the outcome. The results are summarized in Table 1.

TABLE 1

Cutaneous DTH - Experiment 1

| Group | Strain | Test Antigen | Erythema (mm ± SE) | Induration (mm ± SE) |
|---|---|---|---|---|
| A | Sham | r30 | 2.7 ± 1.3 | 0 ± 0 |
| B | BCG | r30 | 5.8 ± 1.4 | 0 ± 0 |
| C | rBCG30 | r30 | 11.8 ± 2.6 | 5.6 ± 3.5 |
| D | rBCG30/hINFγ | r30 | 6.3 ± 1.4 | 0 ± 0 |
| E | rBCG(mbtB) Lo Fe | r30 | 2.0 ± 1.0 | 0 ± 0 |

TABLE 1-continued

Cutaneous DTH - Experiment 1

| Group | Strain | Test Antigen | Erythema (mm ± SE) | Induration (mm ± SE) |
|---|---|---|---|---|
| F | rBCG(mbtB) Hi Fe | r30 | 3.0 ± 1.6 | 0 ± 0 |
| G | rBCG(mbtB)30 Lo Fe | r30 | 14.4 ± 2.3 | 3.6 ± 3.6 |
| H | rBCG(mbtB)30 Hi Fe | r30 | 10.3 ± 1.3 | 4.7 ± 2.1 |

These results showed that sham-immunized animals (Group A) and animals immunized with the parental BCG Tice strain (Group B) had no induration upon testing with r30. Similarly, animals immunized with a growth-restricted vaccine [rBCG(mbtB)] not over-expressing the 30 kDa protein had no induration upon testing with r30, whether the vaccine was grown under high mycobactin J (Group F) or low mycobactin J (Group E) conditions. In contrast, animals immunized with a recombinant BCG strain over-expressing r30 (Group C) had induration in response to r30. Similarly, animals immunized with the growth-restricted strain rBCG(mbtB)30, whether grown under high mycobactin J (Group H) or low mycobactin J (Group G) conditions, showed induration upon testing with r30. Interestingly, the recombinant BCG expressing both r30 and hIFNγ did not show induration upon testing with r30, although it did display some erythema.

3. Protective Immunity to Aerosol Challenge.

Ten weeks after immunization, the remaining animals in Groups A-H were challenged with an aerosol generated from a 10 ml single-cell suspension containing $7.5\times10^4$ colony-forming units (CFU) of *M. tuberculosis*. Prior to challenge, the challenge strain, *M. tuberculosis* Erdman strain (ATCC 35801), had been passaged through outbred guinea pigs to maintain virulence, cultured on 7H11 agar, subjected to gentle sonication to obtain a single cell suspension, and frozen at −70° C. This aerosol dose delivered ~10 live bacilli to the lungs of each animal. The airborne route of infection was used because this is the natural route of infection for pulmonary tuberculosis. A relatively large dose was used so as to induce measurable clinical illness in 100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 weeks and then euthanized. The right lung and spleen of each animal was removed and cultured for CFU of *M. tuberculosis* on Middlebrook 7H11 agar for two weeks at 37° C., 5% $CO_2$-95% air atmosphere. The results of the assay for CFU in the lungs and spleens are shown in Table 2.

TABLE 2

CFU in Lungs and Spleens - Experiment 1

| Group | Strain | Lung (Mean Log CFU ± SE) | Spleen (Mean Log CFU ± SE) |
|---|---|---|---|
| A | Sham | 6.03 ± 0.10 | 5.57 ± 0.17 |
| B | BCG | 4.83 ± 0.12 | 4.20 ± 0.21 |
| C | rBCG30 | 4.04 ± 0.21 | 2.87 ± 0.23 |
| D | rBCG30/hINFγ | 3.57 ± 0.27 | 2.38 ± 0.30 |
| E | rBCG(mbtB) Lo Fe | 4.49 ± 0.19 | 3.69 ± 0.33 |
| F | rBCG(mbtB) Hi Fe | 4.68 ± 0.25 | 4.42 ± 0.24 |
| G | rBCG(mbtB)30 Lo Fe | 4.40 ± 0.28 | 3.17 ± 0.39 |
| H | rBCG(mbtB)30 Hi Fe | 4.42 ± 0.25 | 2.93 ± 0.31 |

These results showed that animals immunized with BCG or any recombinant BCG strain had much lower CFU in the lungs and spleens than the sham immunized animals.

Animals immunized with the recombinant BCG strain secreting both the M. tuberculosis 30 kDa major secretory protein and hIFNγ (rBCG30/hINFγ) had markedly fewer CFU in the lung and spleen than even rBCG30; animals immunized with rBCG30/hINFγ had 0.5 logs fewer CFU in the lung and spleen than rBCG30. Moreover, in the case of animals immunized with rBCG30/hINFγ, 50% of the animals had no detectable CFU in their spleens and thus were scored at the limit of detection of 1.56 logs. In contrast, in the case of rBCG30 immunized animals, only 14% of the animals had no detectable CFU in the spleen. Compared with animals immunized with BCG, animals immunized with rBCG30/hINFγ had 1.3 logs fewer CFU in the lung and 1.8 logs fewer CFU in the spleen.

Surprisingly, animals immunized with the growth-restricted strain rBCG(mbtB) had fewer CFU in the lung than BCG, whether grown in high or low concentrations of mycobactin J before immunization. Remarkably, animals immunized with the growth-restricted recombinant BCG strain over-expressing the M. tuberculosis 30 kDa major secretory protein [rBCG(mbtB)30], whether grown in the presence of high or low amounts of mycobactin J before immunization, showed an impressive reduction in CFU in animal organs compared with BCG. Animals immunized with rBCG(mbtB)30, whether grown in the presence of high or low amounts of iron before immunization, had 0.4 logs fewer CFU in the lungs than BCG-immunized animals; animals immunized with rBCG(mbtB)30 grown in a low amount of mycobactin J before immunization had 1.0 log fewer CFU in the spleen and animals immunized with rBCG(mbtB)30 grown in a high amount of mycobactin J before immunization had 1.3 log fewer CFU in the spleen than BCG-immunized animals. Remarkably, the reduction in spleen CFUs in animals immunized with rBCG(mbtB)30 grown in a high amount of mycobactin J before immunization was comparable to that observed with rBCG30, which is not growth-restricted.

Experiment 2

1. Immunization of Animals

Specific-pathogen free 250-300 g outbred male Hartley strain guinea pigs from Charles River Breeding Laboratories, in groups of 6, were sham-immunized by intradermal administration of buffer or immunized intradermally with $10^3$ or $10^6$ CFU of one of the following strains:

Group A: Sham-immunized (Sham)
Group B: $10^3$ BCG Tice Parental Control (BCG)
Group C: $10^3$ rBCG30 Tice I (pSMT3-MTB30) (rBCG30)
Group D: $10^3$ rBCG30/hINFγ (pSMT3-MTB30; pGB9.2-hINFγ) Tice (rBCG30/hINFγ)
Group E: $10^3$ rBCG30/hGM-CSF(pSMT3-MTB30; pGB9.2-hGM-CSF) Tice (rBCG30/hGM-CSF)
Group F: $10^3$ rBCG30/hIL-2 (pSMT3-MTB30; pGB9.2-hIL-2) Tice (rBCG30/hIL-2)
Group G: $10^3$ rBCG30/hIL-12 (pSMT3-MTB30; pGB9.2-hIL-12) Tice (rBCG30/hIL-12)
Group H: $10^3$ rBCG(panCD)30 (pNBV1-30) Tice ($10^3$ rBCG(panCD)30)
Group I: $10^6$ rBCG(panCD)30 (pNBV1-30) Tice ($10^6$ rBCG(panCD)30)
Group J: $10^3$ rBCG(panCD)30 (pNBV1-30) Tice—Animals fed diet high in pantothenate ($10^3$ rBCG(panCD) 30-diet)
Group K: $10^6$ rBCG(panCD)30 (pNBV1-30) Tice—Animals fed diet high in pantothenate ($10^6$ rBCG(panCD) 30-diet)

2. Cutaneous Delayed-Type Hypersensitivity (DTH) to Purified Recombinant M. tuberculosis 30 kDa Major Secretory Protein (r30)

Five weeks after immunization, 6 guinea pigs in each group were shaved over the back and injected intradermally with 10 μg of purified recombinant M. tuberculosis 30 kDa major secretory protein (r30) in 100 μl phosphate buffered saline. After 24 h, the diameter of erythema and induration was measured. A separate group of animals from the one used in the challenge studies was used for skin-testing to eliminate the possibility that the skin-test itself might influence the outcome. The results are summarized in Table 3.

TABLE 3

Cutaneous DTH - Experiment 2

| Group | Strain | Test Antigen | Erythema (mm ± SE) | Induration (mm ± SE) |
|---|---|---|---|---|
| A | Sham | r30 | 0 ± 0 | 0 ± 0 |
| B | BCG | r30 | 0 ± 0 | 0 ± 0 |
| C | rBCG30 | r30 | 16.5 ± 1.6 | 14.0 ± 3.2 |
| D | rBCG30/hINFγ | r30 | 6.8 ± 1.5 | 1.2 ± 1.2 |
| E | rBCG30/hGM-CSF | r30 | 6.3 ± 1.6 | 3.0 ± 1.9 |
| F | rBCG30/hIL-2 | r30 | 13.5 ± 3.2 | 13.5 ± 3.2 |
| G | rBCG30/hIL-12 | r30 | 5.7 ± 1.9 | 4.3 ± 2.1 |
| H | $10^3$ rBCG(panCD)30 | r30 | 4.3 ± 1.6 | 0 ± 0 |
| I | $10^6$ rBCG(panCD)30 | r30 | 16.1 ± 1.1 | 16.3 ± 1.0 |
| J | $10^3$ rBCG(panCD)30-diet | r30 | 5.8 ± 1.4 | 0 ± 0 |
| K | $10^6$ rBCG(panCD)30-diet | r30 | 15.2 ± 0.8 | 13.0 ± 2.7 |

These results showed that sham-immunized animals (Group A) and animals immunized with the parental BCG Tice strain (Group B) had no erythema or induration upon testing with r30. In contrast, animals immunized with rBCG30 or recombinant BCG strains producing both r30 and a human cytokine, displayed erythema and induration in response to skin-testing. Animals immunized with a high dose of rBCG(panCD)30 requiring pantothenate for growth displayed marked erythema and induration comparable to that of rBCG30. Animals immunized with a low dose of rBCG(panCD)30 requiring pantothenate for growth displayed some erythema but no induration. Interestingly, whether the animals were fed a high or standard amount of pantothenate in their diet did not significantly influence the amount of induration at a given dose of vaccine. Thus, animals immunized with the new strains secreting the 30 kDa major secretory protein in combination with a human immunostimulatory cytokine developed a cell-mediated immune response to r30. In addition, animals immunized with a high vaccine dose of rBCG(panCD)30 developed a cell-mediated immune response to r30.

3. Antibody to Purified Recombinant M. tuberculosis 30 kDa Major Protein (r30)

Blood was obtained from the animals described above immediately after they were euthanized, and the serum was assayed for antibody titer to r30 by ELISA, using Costar (Corning, N.Y.) 96-well EIA/RIA High Binding Plates, r30 at 1 μg/well, guinea pig serum diluted 1:64 to 1:1,024,000, alkaline phosphatase-conjugated goat anti-guinea pig IgG (Sigma, St. Louis, Mo.) at a dilution of 1:1,000, and an Alkaline Phosphatase Substrate Kit (BioRad, Hercules, Calif.). Titers less than 1:64 were scored as 1:32 for statistical purposes. The results are summarized in Table 4.

TABLE 4

Antibody to r30 - Experiment 2

| Group | Strain | Test Antigen | Geometric Mean Titer |
|---|---|---|---|
| A | Sham | r30 | 84 |
| B | BCG | r30 | 127 |
| C | rBCG30 | r30 | 1154 |
| D | rBCG30/hINFγ | r30 | 48 |
| E | rBCG30/hGM-CSF | r30 | 73 |
| F | rBCG30/hIL-2 | r30 | 49 |
| G | rBCG30/hIL-12 | r30 | 37 |
| H | $10^3$ rBCG(panCD)30 | r30 | 32 |
| I | $10^6$ rBCG(panCD)30 | r30 | 110 |
| J | $10^3$ rBCG(panCD)30-diet | r30 | 37 |
| K | $10^6$ rBCG(panCD)30-diet | r30 | 574 |

These results showed that sham-immunized animals (Group A) and animals immunized with the parental BCG Tice strain (Group B) had relatively low antibody titers to r30. In contrast, animals immunized with rBCG30 had a relatively high titer. Interestingly, animals immunized with recombinant BCG expressing r30 and a cytokine had low titers, indicating that the presence of the cytokine resulted in a diminished antibody response.

Animals immunized with a low dose of rBCG(panCD)30 requiring pantothenate for growth had low titers with or without dietary supplementation with pantothenate. Animals immunized with a high dose of the mutant form of rBCG30 requiring pantothenate for growth had a slightly higher antibody titer in the absence of pantothenate dietary supplementation than animals immunized with a low dose of this strain. However, the antibody titer was markedly increased in animals immunized with a high dose of rBCG(panCD)30 requiring pantothenate for growth who were fed a diet rich in pantothenate. The higher titer is consistent with increased survival of the mutant strain in vivo in animals fed pantothenate.

Experiment 3

1. Immunization of Animals

Specific-pathogen free 250-300 g outbred male Hartley strain guinea pigs from Charles River Breeding Laboratories, in groups of 15 or 21, were sham-immunized by intradermal administration of buffer (15 animals total) or immunized intradermally with $10^3$ or $10^6$ CFU of one of the following strains (21 animals/group):

Group A: Sham-immunized (Sham)
Group B: $10^3$ BCG Tice Parental Control (BCG)
Group C: $10^3$ rBCG30 Tice I (pSMT3-MTB30) (rBCG30)
Group D: $10^3$ rBCG30/hINFγ (pSMT3-MTB30; pGB9.2-hINFγ) Tice (rBCG30/hINFγ)
Group E: $10^3$ rBCG/hINFγ (pGB9.2-hINFγ) Tice (rBCG/hINFγ)
Group F: $10^3$ BCG Tice Parental Control—Grown in medium containing Tyloxapol ($10^3$ BCG-Tyl)
Group G: $10^3$ rBCG(mbtB) Tice—Grown in medium containing a high mycobactin J concentration ($10^3$ rBCG (mbtB) Hi Fe)
Group H: $10^3$ rBCG(mbtB)30 II (pNBV1-30) Tice—Grown in medium containing a high mycobactin J concentration ($10^3$ rBCG(mbtB)30 Hi Fe)
Group I: $10^6$ BCG Tice Parental Control—Grown in medium containing Tyloxapol ($10^6$ BCG-Tyl)
Group J: $10^6$ rBCG(mbtB) Tice—Grown in medium containing a high mycobactin J concentration ($10^6$ rBCG (mbtB) Hi Fe).
Group K: $10^6$ rBCG(mbtB)30 II (pNBV1-30) Tice—Grown in medium containing a high mycobactin J concentration ($10^6$ rBCG(mbtB)30 Hi Fe)

In addition, specific-pathogen free 250-300 g outbred male Hartley strain guinea pigs from Charles River Breeding Laboratories, in groups of 9 (group L) or 12 (groups M, N, and O) were sham-immunized by intradermal administration of buffer (9 animals total) or immunized intradermally with $10^3$ CFU of one of the following strains (12 animals/group):

Group L: Sham-immunized (Sham)
Group M: $10^3$ BCG Tice Parental Control (BCG)
Group N: $10^3$ rBCG30 Tice I (pSMT3-MTB30) (rBCG30)
Group O: $10^3$ rBCG30/hINFγ (pSMT3-MTB30; pGB9.2-hINFγ) Tice (rBCG30/hINFγ)

2. Cutaneous Delayed-type Hypersensitivity (DTH) to Purified Recombinant *M. tuberculosis* 30 kDa Major Secretory Protein (r30)

Ten weeks after immunization, 6 guinea pigs in each group were shaved over the back and injected intradermally with 10 µg of purified recombinant *M. tuberculosis* 30 kDa major secretory protein (r30) in 100 µl phosphate buffered saline. After 24 h, the diameter of erythema and induration was measured. A separate group of animals from the one used in the challenge studies—see below—was used for skin-testing to eliminate the possibility that the skin-test itself might influence the outcome. The results are summarized in Table 5.

TABLE 5

Cutaneous DTH - Experiment 3

| Group | Strain | Test Antigen | Erythema (mm ± SE) | Induration (mm ± SE) |
|---|---|---|---|---|
| A | Sham | r30 | 2.1 ± 1.0 | 0 ± 0 |
| B | BCG | r30 | 5.0 ± 1.3 | 0 ± 0 |
| C | rBCG30 | r30 | 17.8 ± 2.1 | 16.5 ± 3.4 |
| D | rBCG30/hINFγ | r30 | 4.3 ± 1.6 | 0 ± 0 |
| E | rBCG/hINFγ | r30 | 6.6 ± 2.5 | 0 ± 0 |
| F | $10^3$ BCG-Tyl | r30 | 7.3 ± 1.6 | 1.7 ± 1.7 |
| G | $10^3$rBCG(mbtB) Hi Fe | r30 | 1.5 ± 1.0 | 0 ± 0 |
| H | $10^3$rBCG(mbtB)30 Hi Fe | r30 | 8.8 ± 2.2 | 0 ± 0 |
| I | $10^6$BCG-Tyl | r30 | 4.0 ± 2.2 | 0 ± 0 |
| J | $10^6$rBCG(mbtB) Hi Fe | r30 | 0 ± 0 | 0 ± 0 |
| K | $10^6$rBCG(mbtB)30 Hi Fe | r30 | 15.0 ± 0.8 | 10.3 ± 3.3 |

These results showed that sham-immunized animals (Group A) and animals immunized with the parental BCG Tice strain (Groups B, F, and I) had little or no induration upon testing with r30 whether the strain was grown in medium containing tyloxapol or not and whether or not a high dose was administered. Tyloxapol was used to allow solubilization of mycobactin J with the rBCG(mbtB) and rBCG (mbtB)30 vaccines. It was also added to BCG in some of these experiments as a control. Tyloxapol had no influence on protection.

Similarly, animals immunized with a growth-restricted vaccine [rBCG(mbtB)] not over-expressing the 30 kDa protein had no induration upon testing with r30, whether a low dose (Group G) or high dose (Group J) of the vaccine was administered. In contrast, animals immunized with a recombinant BCG strain over-expressing r30 (Group C) had induration in response to r30. Similarly, animals immunized with the growth-restricted strain rBCG(mbtB)30, when administered as a high dose (Group K) showed induration upon testing with r30. Animals immunized with a low dose of the growth-restricted strain rBCG(mbtB)30 (Group H) showed no induration upon testing with r30. Interestingly, as previously observed, the recombinant BCG expressing both r30 and hIFNγ (Group D) did not show induration upon testing with r30, although it did display some erythema.

3. Protective Immunity to Aerosol Challenge. Part A:

Ten weeks after immunization, the remaining animals in Groups A-K were challenged with an aerosol generated from a 10 ml single-cell suspension containing $7.5\times10^4$ CFU of *M. tuberculosis*. This aerosol dose delivered ~10 live bacilli to the lungs of each animal. The airborne route of infection was used because this is the natural route of infection for pulmonary tuberculosis. A relatively large dose was used so as to induce measurable clinical illness in 100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 weeks and then euthanized. The right lung and spleen of each animal was removed and cultured for CFU of *M. tuberculosis* on Middlebrook 7H11 agar for two weeks at 37° C., 5% $CO_2$-95% air atmosphere. The results of the assay for CFU in the lungs and spleens are shown in Table 6.

TABLE 6

CFU in Lungs and Spleens - Experiment 3, Part A

| Group | Strain | Lung (Mean Log CFU ± SE) | Spleen (Mean Log CFU ± SE) |
|---|---|---|---|
| A | Sham | 6.63 ± 0.22 | 6.41 ± 0.22 |
| B | BCG | 5.17 ± 0.09 | 4.48 ± 0.06 |
| C | rBCG30 | 4.23 ± 0.13 | 3.47 ± 0.09 |
| D | rBCG30/hINFγ | 4.03 ± 0.09 | 2.57 ± 0.26 |
| E | rBCG/hINFγ | 5.11 ± 0.07 | 4.39 ± 0.05 |
| F | $10^3$ BCG-Tyl. | 4.96 ± 0.08 | 4.59 ± 0.07 |
| G | $10^3$rBCG(mbtB) Hi Fe | 5.37 ± 0.16 | 4.79 ± 0.18 |
| H | $10^3$rBCG(mbtB)30 Hi Fe | 5.01 ± 0.16 | 4.63 ± 0.26 |
| I | $10^6$BCG-Tyl. | 5.17 ± 0.09 | 4.31 ± 0.08 |
| J | $10^6$rBCG(mbtB) Hi Fe | 4.83 ± 0.12 | 4.23 ± 0.12 |
| K | $10^6$rBCG(mbtB)30 Hi Fe | 4.56 ± 0.21 | 3.94 ± 0.21 |

These results showed that animals immunized with BCG or any recombinant BCG strain had much lower CFU in the lungs and spleens than the sham immunized animals.

Animals immunized with the recombinant BCG strain secreting both the *M. tuberculosis* 30 kDa major secretory protein and hIFNγ (rBCG30/hINFγ) had markedly fewer CFU in the lung and spleen than animals immunized with rBCG30; animals immunized with rBCG30/hINFγ had 0.2 logs fewer CFU in the lung and 0.9 logs fewer CFU in the spleen than rBCG30-immunized animals.

Importantly, animals immunized with the recombinant BCG vaccine secreting only hIFNγ did not show protection significantly different from BCG. Hence, it was the co-expression of both the 30 kDa protein and hIFNγ that was necessary for the superior efficacy of the rBCG30/hINFγ vaccine.

Furthermore, animals immunized with the high dose of the growth-restricted recombinant BCG strain over-expressing the *M. tuberculosis* 30 kDa major secretory protein [rBCG (mbtB)30]) showed an impressive reduction in CFU in animal organs compared with BCG, whether or not the BCG vaccine was grown in tyloxapol. There was no significant difference in potency of BCG vaccines grown in the presence or the absence of tyloxapol.

4. Protective Immunity to Aerosol Challenge. Part B:

Twenty weeks after immunization, the animals in Groups L-O were challenged with an aerosol generated from a 10 ml single-cell suspension containing $7.5\times10^4$ CFU of *M. tuberculosis*. This aerosol dose delivered ~10 live bacilli to the lungs of each animal. The airborne route of infection was used because this is the natural route of infection for pulmonary tuberculosis. A relatively large dose was used so as to induce measurable clinical illness in 100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 weeks and then euthanized. The right lung and spleen of each animal was removed and cultured for CFU of *M. tuberculosis* on Middlebrook 7H11 agar for two weeks at 37° C., 5% $CO_2$-95% air atmosphere. The results of the assay for CFU in the lungs and spleens are shown in Table 7.

TABLE 7

CFU in Lungs and Spleens - Experiment 3, Part B

| Group | Strain | Lung (Mean Log CFU ± SE) | Spleen (Mean Log CFU ± SE) |
|---|---|---|---|
| A | Sham | 6.46 ± 0.08 | 6.07 ± 0.01 |
| B | BCG | 4.06 ± 0.12 | 3.51 ± 0.09 |
| C | rBCG30 | 3.33 ± 0.10 | 2.94 ± 0.08 |
| D | rBCG30/hINFγ | 1.74 ± 0.06 | 1.57 ± 0.09 |

In the case of animals immunized with rBCG30/hINFγ, 5 of 12 animals had no detectable CFU in their lungs and 7 of 12 animals had no CFU in their spleens and thus were scored at the limit of detection of 1.6 logs in the lungs and 1.3 logs in the spleen. In contrast, in the case of rBCG30 immunized animals, none of the animals had no detectable CFU in the lungs or spleen. Compared with animals immunized with rBCG30, animals immunized with rBCG30/hINFγ had 1.6 logs fewer CFU in the lung and 1.4 logs fewer CFU in the spleen. Compared with animals immunized with BCG, animals immunized with rBCG30/hINFγ had 2.3 logs fewer CFU in the lung and 1.9 logs fewer CFU in the spleen.

Example 2 rBCGs Expressing Proteins Integrated into Genomic DNA

In another embodiment of the present invention, the genes encoding immunogenic intracellular pathogen proteins and/or cytokines can be integrated into the chromosome. For example, rBCG strains have been generated that over-express the *M. tuberculosis* 30 kDa protein from the chromosome through an allelic exchange procedure. A cassette containing the fbpB gene (encoding the 30 kDa protein) with expression driven from the rrs promoter was cloned into a wild-type glnA1 locus, just downstream of glnA1. This glnA1 locus with the fbpB insertion was cloned into phEX2 (a derivative of phEX1, itself a derivative of phAE87 [Bardarov et al., Microbiol. 148:3007-3017, 2002]) and specialized transducing phage was prepared by electroporating the plasmid into *M. smegmatis*. The phage was used to infect BCG strains and clones over-expressing the 30 kDa protein were selected.

Example 3

Recombinant BCG Expressing Interferon Gamma (IFNγ)

The first approach, using a typical Sec signal peptide to secrete hIFNγ, resulted in a strain with unstable expression and secretion of biologically active hIFNγ. Therefore, recombinant BCG vaccines were generated that expressed and secreted mycobacterial codon optimized hIFNγ using twin-arginine translocation (Tat) signal peptides from plcB (MTRRQFFAKAAAATTAGAFMSLAGPIIEKAYG, SEQ ID NO:1), phoD (MAYDSRFDEWVQKLKEESFQNNTFDRRKFIQGAGKIAGLSLGLTIAQSVGAFEV, SEQ ID NO:2), and torA (MNNNDLFQASRRRFLAQLGGLTVAGMLGPSLLTPRRATA, SEQ ID NO:3). Proteins secreted by the Tat system are secreted after first folding in the cytoplasm, in contrast to the proteins secreted by the Sec system, which are not folded prior to secretion. As a control, intracellular hIFNγ (i.e. without a signal peptide) was also expressed to confirm the generation of a stable strain expressing full-length hIFNγ, uncomplicated by the difficulties inherent with secretion of a foreign protein. In addition, a potentially more stable, covalent dimer version of hIFNγ (two monomers joined by a peptide linker, PVPSTPPTPSPSTPTPS, SEQ ID NO:4 [Lunn et al. J. Biol. Chem. 267:17920-4, 1992]), was also expressed both intracellularly as well as secreted using Tat signal peptides. Some constructs also contained a c-myc epitope tag fused to the C-terminus of IFNγ. As IFNγ is species specific, and hIFNγ is not biologically active in the mouse, mycobacterial codon optimized mIFNγ versions of all of the hIFNγ constructs described above were generated. hIFNγ and mIFNγ were expressed from plasmids in both BCG Tice and rBCG30-ARMF-II Tice, a recombinant BCG expressing the M. tuberculosis 30 kDa major secretory protein (Antigen 85B) from the chromosome and which is Antibiotic Resistance Marker Free. rBCG30-ARMF-II Tice overexpresses Antigen 85B at levels equal to or somewhat greater than rBCG30 and expression is very stable (no change after 120 generations of growth in broth culture) (U.S. patent application Ser. No. 12/664,485 which is incorporated by reference herein for all it discloses regarding rBCG immunogenic compositions). This new rBCG30 strain was used as a host, along with parental BCG, for expression of IFNγ constructs, allowing use of the same expression plasmid in both strains.

BCG vaccines were generated by electroporating recombinant expression plasmids (derived from pNBV1 or pRE1, a pNBV1 derivative) into the BCG Tice wild-type strain and the rBCG30-ARMF-II Tice strain. The expression plasmids contained a mycobacterial promoter for expression, in some cases a Tat signal peptide sequence for secretion, and the coding region of a mycobacterial codon optimized IFNγ gene (hIFNγ or mIFNγ). Recombinant clones were selected on 7H10 agar and in 7H9 liquid culture containing 50 µg/mL hygromycin. Clones were screened for expression and secretion of IFNγ; the rBCG30-ARMF-II Tice clones were also screened for the secretion of recombinant M. tuberculosis 30 kDa major secretory protein. For the analyses of protein expression, culture filtrates and boiled cell pellets were analyzed by Coomassie Blue staining of SDS-PAGE gels and/or by immunoblotting to measure the amount of IFNγ and 30 kDa major secretory protein each recombinant vaccine expresses.

Example 4

Constructs Expressing hIFNγ and a Covalent Dimer of hIFNγ (hIFNγ-CD)

These vaccines contain a recombinant pNBV1 plasmid expressing hIFNγ or hIFNγ-CD from the promoter of the 23.5 kDa protein gene (mpt64 or Rv1980) of M. tuberculosis. For improved expression and stability of foreign gene expression, the hIFNγ gene was codon optimized for expression in mycobacteria (DNA2.0). The covalent dimer was constructed by joining two copies of the gene with a sequence for a peptide linker. Vaccines constructed from the rBCG30-ARMF-II Tice strain also overexpress and secrete the M. tuberculosis 30 kDa major secretory protein (Antigen 85B) from the chromosome in addition to expressing hIFNγ from the plasmid. Constructs expressing and secreting hIFNγ and hIFNγ-CD are as follows:

a. BCG Tice pNBV1-P23.5-plcB-SP(+3)-co-hIFNγ-v2
b. BCG Tice pNBV1-P23.5-torA-SP(+4)-co-h IFNγ-v2-c-myc
c. BCG Tice pNBV1-P23.5-phoD-SP(+6)-co-h IFNγ-v2
d. BCG Tice pNBV1-P23.5-plcB-SP(+3)-co-hIFNγ-v2-CD
e. BCG Tice pNBV1-P23.5-torA-SP-co-hIFNγ-v2-CD
f. rBCG30-ARMF-II Tice pNBV1-P23.5-plcB-SP(+3)-co-hIFNγ-v2
g. rBCG30-ARMF-II Tice pNBV1-P23.5-phoD-SP(+6)-co-h IFNγ-v2
h. rBCG30-ARMF-II Tice pNBV1-P23.5-torA-SP-co-hIFNγ-v2

Figure 8:
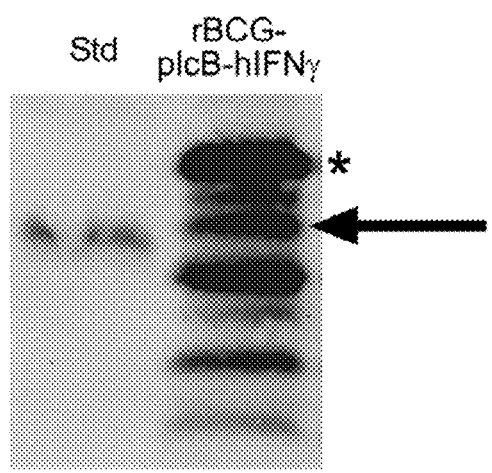
Figure 9:
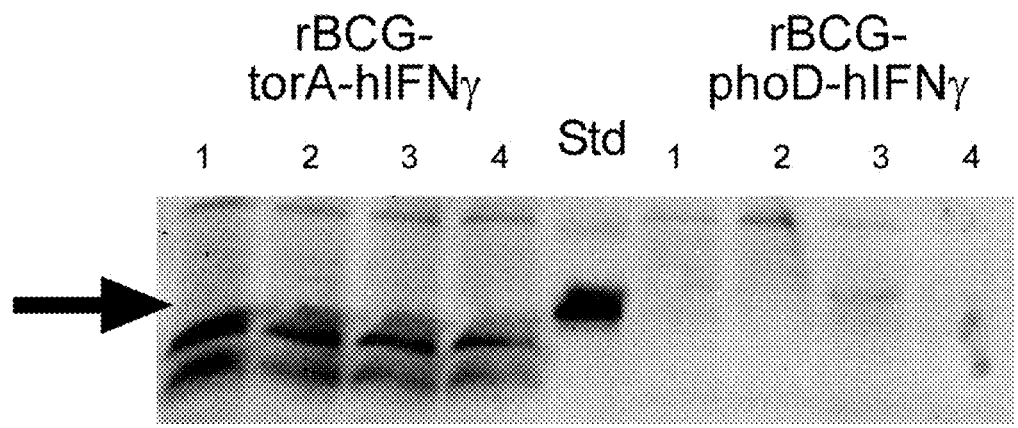
Figure 10:
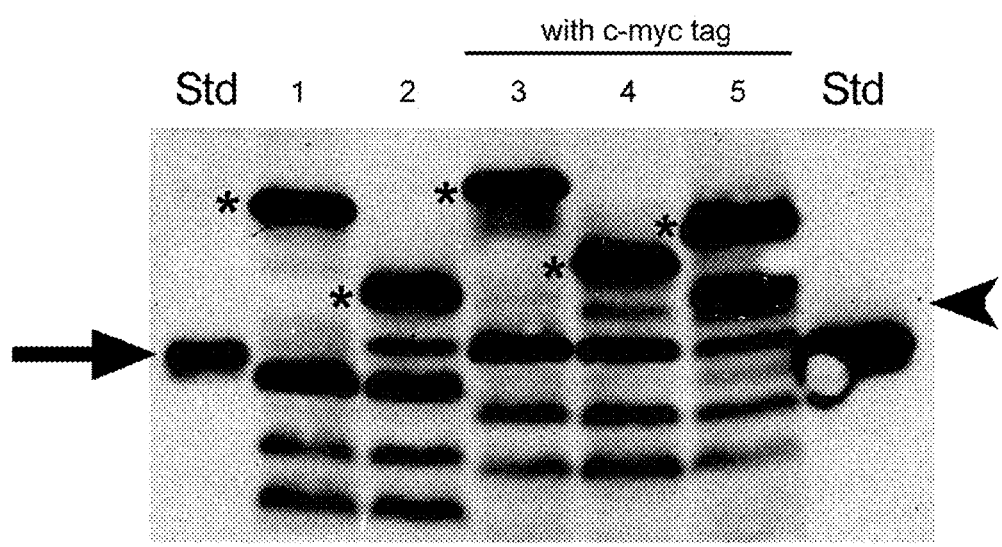
Figure 11:
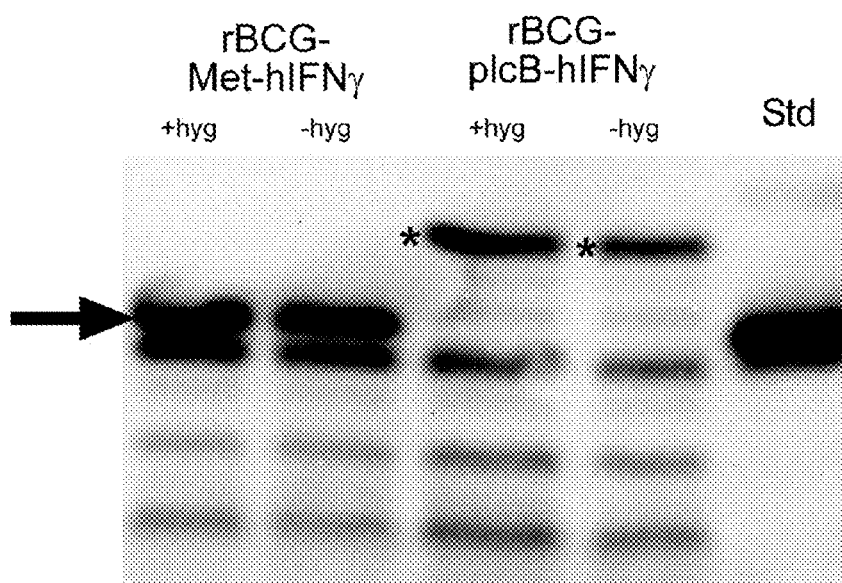

Due to unanticipated difficulty in obtaining stable secretion of biologically active hIFNγ with a typical Sec signal peptide, secretion was attempted using an N-terminal twin-arginine translocation (Tat) secretion signal (from the M. tuberculosis plcB, the Bacillus subtilis phoD, and the Escherichia coli torA genes) fused to the hIFNγ gene. In contrast to the Sec system, that directs the secretion of proteins in an unfolded state, the Tat system secretes proteins in their folded state. Sequence encoding for additional amino acids from the N-terminus of the mature PlcB (3 additional amino acids), mature PhoD (6 additional amino acids), and mature TorA (4 additional amino acids) was included to enhance cleavage of the signal peptide following secretion. Only the construct with the PlcB signal peptide produced full length mature hIFNγ (FIG. 8). Surprisingly, the recombinant BCG vaccines using the TorA and PhoD signal peptides yielded no full length mature hIFNγ (FIG. 9) in contrast to results with the same expression plasmids in the fast growing mycobacterium, M. smegmatis (FIG. 10). In particular, M. smegmatis expressing hIFNγ from plasmid pNBV1-P23.5-torA-SP(+4)-co-hIFNγ-v2-c-myc, had the greatest amount of full length mature hIFNγ of all the constructs tested, but recombinant BCG expressing hIFNγ from this same plasmid only produced breakdown products (FIG. 9). Although no clones were obtained of any BCG Tice expressing hIFNγ using the PhoD signal peptide (FIG. 9), rBCG30-ARMF-II Tice strain clones expressing hIFNγ using the PhoD signal peptide were obtained (not shown). The expression profile for these clones was similar to the profile of constructs expressing hIFNγ with the PlcB signal peptide (FIG. 8)—the predominant species of hIFNγ did not have the signal peptide cleaved off and a minor portion was the mature protein. Expression of full length mature hIFNγ from BCG Tice pNBV1-P23.5-plcB-SP(+3)-co-hIFNγ-v2 was stable for at least 4 subcultures (~40 generations) even in the absence of selective pressure on the plasmid (FIG. 11). A full length mature covalent dimer of hIFNγ (hIFNγ-CD) was also successfully expressed using the PlcB signal peptide by BCG Tice pNBV1-P23.5-plcB-SP(+3)-co-hIFNγ-v2-OD, similar to expression of the single gene (FIG. 12). Constructs expressing intracellular hIFNγ and hIFNγ-CD are as follows:

a. BCG Tice pNBV1-P23.5-Met-co-hIFNγ-v2
b. BCG Tice pNBV1-P23.5-Met-co-hIFNγ-v2-CD
c. rBCG30-ARMF-II Tice pNBV1-P23.5-Met-co-hIFNγ-v2
d. rBCG30-ARMF-II Tice pNBV1-P23.5-Met-co-hIFNγ-v2-CD These vaccines express mature hIFNγ (and hIFNγ-CD) intracellularly (i.e. there is no secretion signal). Because secretion by the Sec system led to unstable expression of biologically active hIFNγ, and secretion using the PlcB Tat signal peptide, although producing the correct size protein for mature hIFNγ, also produced a large amount of breakdown products, these vaccines were initially intended as controls simply to determine if BCG could stably express hIFNγ of the correct size, uncomplicated by the difficulties with secretion. Indeed, they demonstrated that large amounts of the correct size hIFNγ could be produced by BCG (FIG. 13). Expression of full length mature hIFNγ was stable for at least 4 subcultures (~40 generations) even in the absence of selective pressure on the plasmid (FIG. 11). A full length mature covalent dimer of hIFNγ (hIFNγ-CD) was also successfully expressed without a signal peptide by BCG Tice pNBV1-P23.5-Met-co-hIFNγ-v2-CD, similar to expression of the single gene (FIG. 12). Indicative of its greater stability, the covalent dimer was present in the culture filtrate at higher levels than the non-covalent dimer (FIG. 12; compare 1 and 3). Likewise, the greater expression of full length mature hIFNγ and hIFNγ-CD without a signal peptide compared with that produced using a signal peptide can account for their higher levels observed in the culture filtrate (FIG. 12; hIFNγ: compare 1 and 2, hIFNγ-CD, compare 3 and 4).

Quite unexpectedly, vaccines expressing hIFNγ without a secretion signal demonstrated biological activity in several assays and were even somewhat better than the vaccine expressing and secreting hIFNγ via the Tat system (FIG. 17), suggesting that hIFNγ expressed intracellularly must be released in sufficient quantity from the recombinant BCG organisms inside the host cell to interact with and affect the host cell.

Example 5

Constructs Expressing mIFNγ and a Covalent Dimer of mIFNγ (mIFNγ-CD)

These vaccines contain a recombinant pNBV1 plasmid or pRE1 plasmid (a pNBV1 derivative) expressing mIFNγ or mIFNγ-CD from the promoter of the 23.5 kDa protein gene (mpt64 or Rv1980) or a shortened derivative of the rrs (rrnS or 16S ribosomal RNA gene) promoter lacking the boxA, boxB, and boxC elements (U.S. patent application Ser. No. 12/664, 485 which is incorporated by reference herein for all it discloses regarding rBCG immunogenic compositions); both promoters are from *M. tuberculosis*. For improved expression and stability of foreign gene expression, the mIFNγ gene was codon optimized for expression in mycobacteria (DNA2.0). The covalent dimer was constructed by joining two copies of the gene with a sequence for a peptide linker. A mIFNγ-CD gene with a modified linker (mIFNγ-CD-ML) was also constructed. Vaccines constructed from the rBCG30-ARMF-II Tice strain also overexpress and secrete the *M. tuberculosis* 30 kDa major secretory protein (Antigen 85B) from the chromosome in addition to expressing mIFNγ from the plasmid. rBCG30p-Met-co-mIFNγ Tice pRE13.2 expresses and secretes the *M. tuberculosis* 30 kDa major secretory protein from the same plasmid used to express mIFNγ. Constructs expressing and secreting mIFNγ and mIFNγ-CD are as follows:
    a. BCG Tice pNBV1-P23.5-plcB-SP(+3)-Met-co-mIFNγ
    b. BCG Tice pNBV1-P23.5-phoD-SP(+6)-Met-co-mIFNγ
    c. rBCG30-ARMF-II Tice pNBV1-P23.5-plcB-SP(+3)-Met-co-mIFNγ
    d. rBCG30-ARMF-II Tice pNBV1-P23.5-phoD-SP(+6)-Met-co-mIFNγ

As hIFNγ is species-specific and not biologically active in the mouse, mIFNγ versions of the hIFNγ constructs described above in Example 4 were generated. In contrast to the recombinant BCG vaccine designed to express hIFNγ using the PhoD signal peptide (FIG. 9), the analogous construct with mIFNγ was successfully expressed, although only a small portion of the total expressed mIFNγ was present as the full length mature protein (FIG. 14). Expression of mIFNγ using the PlcB signal peptide (FIG. 14) was similar to the analogous recombinant BCG vaccines expressing hIFNγ with a PlcB signal peptide (FIGS. 8, 11, and 12) in that the major band still contained the signal peptide and a minor portion was present as the mature protein. Constructs expressing intracellular mIFNγ and mIFNγ-CD are as follows:
    a. BCG Tice pRE1-Prrs(short)-Met-co-mIFNγ
    b. BCG Tice pRE1-Prrs(short)-Met-co-mIFNγ-CD
    c. BCG Tice pRE1-Prrs(short)-Met-co-mIFNγ-CD-ML
    d. rBCG30p-Met-co-mIFNγ Tice pRE13.2
    e. rBCG30-ARMF-II Tice pRE1-Prrs(short)-Met-co-mIFNγ
    f. rBCG30-ARMF-II Tice pRE1-Prrs(short)-Met-co-mIFNγ-CD
    g. rBCG30-ARMF-II Tice pRE1-Prrs(short)-Met-co-mIFNγ-CD-ML mIFNγ versions of the hIFNγ constructs described above in Example 4 were generated. Whereas the hIFNγ constructs used the promoter from the 23.5 kDa protein gene (mpt64 or Rv1980), the mIFNγ constructs listed here used an even stronger promoter, a shortened derivative of the rrs (rrnS or 16S ribosomal RNA gene) promoter lacking the boxA, boxB, and boxC elements. As with recombinant BCG expressing hIFNγ, recombinant BCG expressing mIFNγ without a signal peptide produced relatively large amounts of the correct size mIFNγ and expression was stable for at least 2 subcultures (~20 generations) even in the absence of selective pressure on the plasmid (FIG. 15). A full length mature covalent dimer of mIFNγ (mIFNγ-CD) or mIFNγ-CD with a modified linker (mIFNγ-CD-ML) were also successfully expressed without a signal peptide by recombinant BCG strains (FIG. 16), as was observed for the covalent dimer of hIFNγ (hIFNγ-CD) (FIG. 12).

Example 6

Biological Activity of Recombinant BCG Expressing IFNγ

IFNγ, a product of NK cells, CD8+ T cells, and the Th1 subclass of CD4+ T cells is a homodimer that exerts its effects via receptors found on virtually all cells. Among its effects are the induction of an IFNγ transcriptome and the upregulation of class I and II MHC molecules on antigen presenting cells. These are known effects of biologically active IFNγ when it is added to cells in tissue culture.

BCG, like *M. tuberculosis*, arrests the maturation of its phagosome in macrophages and resides in a phagosome that interacts with early and late endosomes within the host cell.

A. Induction of IFNγ Transcriptome in Host Cells

Figure 18:
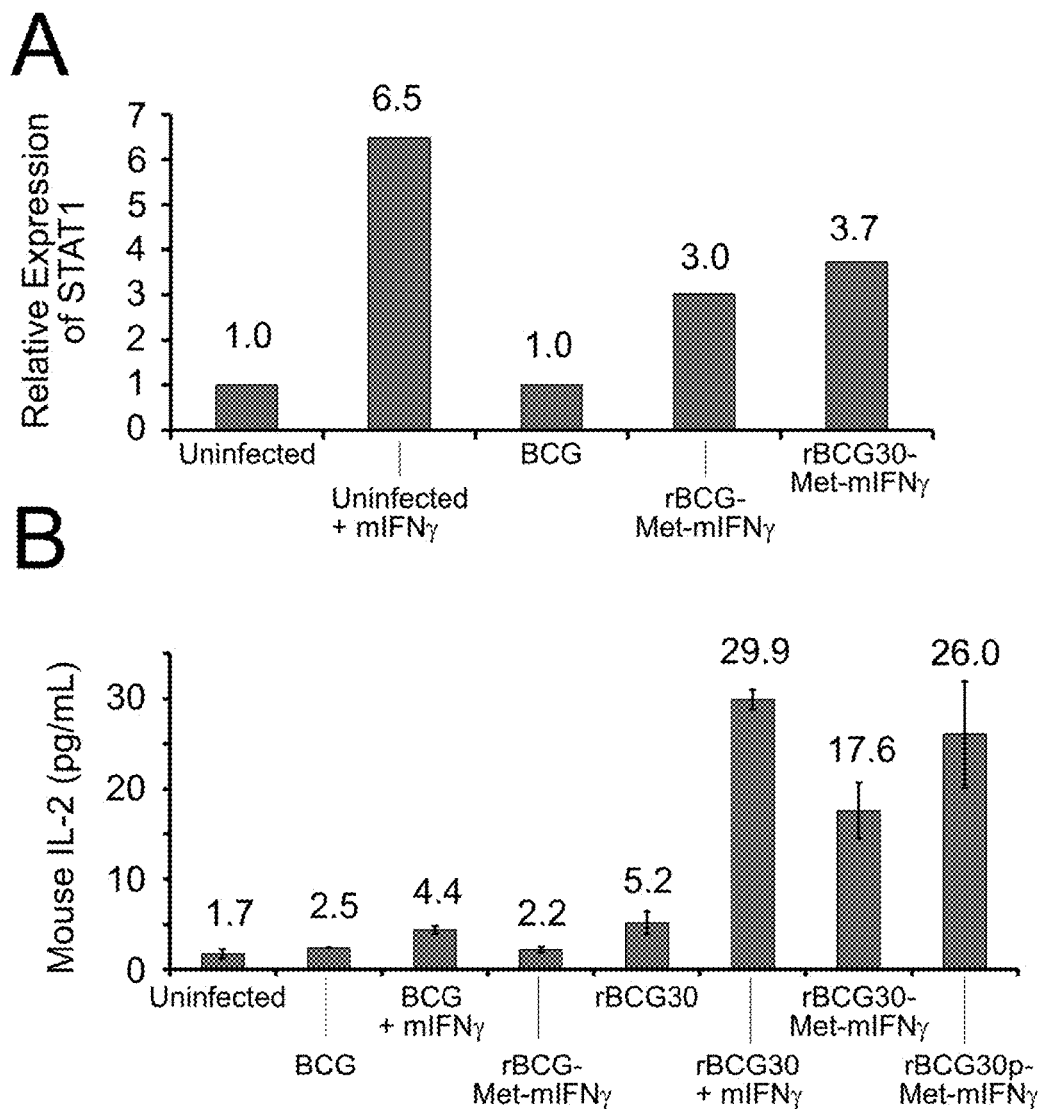

To determine if rBCG expressing IFNγ could induce an IFNγ transcriptome in the infected host cell, the induction of STAT1 was assayed. STAT1 is an important IFNγ-activated transcription factor and is known to be upregulated in macrophages following exposure to exogenous IFNγ. To determine if rBCG expressing IFNγ could induce STAT1 in host cells, a qRT-PCR assay was established using the human THP-1 macrophage-like cell line to measure the biological activity of our rBCG strains expressing hIFNγ and using mouse macrophage cell lines (J774.A1 and RAW264.7) to measure the biological activity of our rBCG strains expressing mIFNγ. Monolayers in 24-well plates were infected at various multiplicities of infection (MOI, from 1 to 50) of recombinant BCG, or parental BCG as a negative control, and for various durations (from 1 to 3 days). Pure IFNγ protein (human or mouse) was used as a positive control. RNA was isolated from monolayers, converted to cDNA, and analyzed by qRT-PCR using TaqMan Gene Expression assays for STAT1 and ACTB (for normalization). STAT1 was consistently induced in cells infected with rBCG strains expressing IFNγ (FIG. 17A and FIG. 18A). Thus, remarkably, IFNγ expressed by rBCG within its phagosome inside host cells is able to induce an IFNγ transcriptome.

B. Upregulation of MHC Class I and MHC Class II Surface Markers on Host Cells

Having established that IFNγ produced by rBCG within the host cell could induce a relevant molecule of the IFNγ transcriptome of the host cell, it was determined if such IFNγ could also upregulate expression of MHC class I and II molecules on the infected host cell. To determine this, a flow cytometry assay of MHC class I and II expression of host cells infected with rBCG expressing IFNγ was established. Human peripheral blood mononuclear cells were allowed to adhere to tissue culture wells for 90 min, washed to remove non-adherent cells, and then infected with recombinant BCG, or parental BCG as a negative control, at a MOI of 1 for 36 hours. Pure hIFNγ protein was used as a positive control. Monocytes were labeled with specific antibodies against human MHC class I and MHC class II molecules, as well as the monocyte marker CD14, and analyzed by flow cytometry. Monocytes infected with rBCG30-Met-hIFNγ showed a significant increase in MHC class I (not shown) and MHC class II surface molecules relative to monocytes infected with parental BCG (FIG. 10B). The magnitude of the response was similar to that of monocytes treated with pure hIFNγ protein.

C. Antigen Presentation

Having established that IFNγ produced by rBCG within the host cell could induce a relevant molecule of the IFNγ transcriptome of the host cell and upregulate class I and II MHC molecules on the infected host cell, would this result in enhanced antigen presentation of BCG antigens by the host cell. To do so, T-cell hybridomas specific for MHC-peptide complexes on human and mouse cells were employed.

T-cell hybridomas have been developed to measure specific peptide-MHC complexes, and we have obtained T-cell hybridoma cell-lines that recognize a peptide from the *M. tuberculosis* 30-kDa major secretory protein complexed with MHC class II (HLA-DR1) on human and mouse cells. This is a powerful assay as it involves a T-cell recognizing a specific epitope of an antigen complexed to an MHC molecule on the surface of an antigen presenting cell and producing a biological response (secretion of IL-2). The amount of IL-2 produced is directly proportional to the number of specific MHC-peptide complexes on the host cell surface, and thus this is a measure of antigen presentation. Therefore, to assess antigen presentation by our rBCG vaccines, this assay using the human THP-1 macrophage-like cell line was used.

THP-1 monolayers in 96-well plates were infected with recombinant BCG, or parental BCG as a negative control, at an MOI of 20 for 1 or 2 days. Pure hIFNγ protein was used as a positive control. The cells were fixed, the DB1 T-hybridoma cell-line added for 20-24 hours, and amount of murine IL-2 secreted into the medium was measured by ELISA. THP-1 cells incubated with rBCG30 showed little or no increase in presentation of the 30 kDa protein epitope (mean of 3-fold in 3 experiments) compared with BCG infected THP-1 cells (FIG. 17C). Likewise, treatment of BCG infected THP-1 cells with pure hIFNγ or infection of THP-1 cells with a unimodal BCG expressing biologically active hIFNγ resulted in only a small increase in presentation of the 30 kDa protein epitope (mean of 3-fold in 3 experiments) compared with BCG infected THP-1 cells. Surprisingly, and in marked contrast, infection of THP-1 cells with the bimodal vaccine rBCG30-Met-hIFNγ resulted in a remarkable 35-fold increase in presentation of the 30 kDa protein epitope compared with BCG infected cells (mean of 3 experiments). Thus, unexpectedly, the two recombinant molecules produced by the bimodal vaccine (rBCG30-Met-hIFNγ) acted synergistically to enhance antigen presentation, i.e. the increase in antigen presentation induced by rBCG30-Met-hIFNγ greatly exceeds the increase induced by the unimodal vaccines rBCG30 and rBCG-Met-hIFNγ. This indicated that it is the co-expression of the molecules that underlies the enhanced antigen presentation. It also was quite unexpected that the rBCG30 vaccine coexpressing, but not actively secreting, hIFNγ (i.e. without a signal peptide) not only demonstrated biological activity, but was in fact superior to the rBCG30 vaccine secreting hIFNγ using a signal peptide (FIG. 17C).

A similar study was performed using mouse macrophages and a T-cell hybridoma specific for an MHC-peptide complex on mouse macrophages. Similar to rBCG-Met-hIFNγ, the bimodal vaccine expressing mIFNγ (rBCG30-Met-mIFNγ) also demonstrated synergistically enhanced antigen presentation in mouse bone marrow macrophages (FIG. 18B). This indicated that in these experiments, as in the experiments with vaccines expressing hIFNγ, it is the co-expression of IFNγ and the immunodominant molecule that underlies the enhanced antigen presentation.

Example 7

Recombinant BCG Expressing IFNγ Induces Protective Immunity

Having determined that bimodal vaccines expressing IFNγ and overexpressing the 30 kDa protein result in enhanced antigen presentation on host cells, it was determined if such vaccines would induce greater protective immunity. A murine model of pulmonary tuberculosis was used to investigate this and rBCG vaccines expressing murine IFNγ, which is species-specific, were studied.

In the mouse model, animals are not immunized (Sham-control) or immunized with BCG vaccine or one or another rBCG vaccine and later challenged by aerosol with highly virulent *M. tuberculosis*. The aerosol route was chosen because this is the natural route of infection for pulmonary tuberculosis.

Specific-pathogen free 6-week old female C57BL/6 mice from Charles River Breeding Laboratories, in groups of 8, were sham-immunized by intradermal administration of buffer or immunized intradermally with $10^6$ CFU of one of the following strains (8 animals/group) in a total volume of 50 μl:

Group A: Sham-immunized (Sham)

Group B: BCG Tice Parental Control (BCG)

Group C: rBCG30-ARMF-II Tice (rBCG30-ARMF)

Group D: BCG Tice pRE1-Prrs(short)-Met-co-mIFNγ (rBCG-Met-mIFNγ)

Group E: rBCG30-ARMF-II Tice pRE1-Prrs(short)-Met-co-mIFNγ (rBCG30-Met-mIFNγ)

Twelve weeks after immunization, animals were challenged with an aerosol generated from a 7.5 ml single-cell suspension containing $1.5\times10^6$ colony-forming units (CFU) of *M. tuberculosis*/ml. Prior to challenge, the challenge strain, *M. tuberculosis* Erdman strain [ATCC 35801], had been passaged through outbred guinea pigs to maintain virulence, cultured on 7H11 agar, subjected to gentle sonication to obtain a single cell suspension, and frozen at −70° C. This aerosol dose delivers 100-200 live bacilli to the lungs of each animal. The animals were observed for illness and weighed weekly for 10 weeks and then euthanized. The lung and spleen of each animal was removed and cultured for CFU of *M. tuberculosis* on Middlebrook 7H11 agar for two to three weeks at 37° C., 5% $CO_2$-95% air atmosphere. The results of the assay for CFU in the lungs and spleens are shown in Table 8.

TABLE 8

CFU in Lungs and Spleens - Experiment 1

| Group | Strain | Lung (Mean Log CFU ± SE) | Spleen (Mean Log CFU ± SE) |
|---|---|---|---|
| A | Sham | 5.84 ± 0.16 | 4.68 ± 0.14 |
| B | BCG Tice | 5.33 ± 0.09 | 4.41 ± 0.10 |
| C | rBCG30-ARMF | 5.18 ± 0.08 | 4.14 ± 0.09 |
| D | rBCG-Met-mIFNγ | 5.39 ± 0.04 | 4.43 ± 0.04 |
| E | rBCG30-Met-mIFNγ | 4.93 ± 0.07 | 3.95 ± 0.06 |

These results showed that animals immunized with BCG or any recombinant BCG strain had lower CFU in the lungs and spleens than the sham immunized animals.

Animals immunized with the recombinant BCG strain secreting the *M. tuberculosis* 30 kDa major secretory protein (rBCG30-ARMF) had fewer CFU in the lung (0.15 logs fewer) and spleen (0.27 logs fewer) than animals immunized with BCG. Remarkably, animals immunized with the recombinant BCG strain secreting both the *M. tuberculosis* 30 kDa major secretory protein and expressing intracellular mIFNγ (rBCG30-Met-mIFNγ) had fewer CFU in the lung and spleen than even rBCG30-ARMF; animals immunized with rBCG30-Met-mIFNγ had 0.25 logs fewer CFU in the lung (P=0.04, ANOVA) and 0.19 logs fewer CFU in the spleen (P=0.1, ANOVA) than animals immunized with rBCG30-ARMF. Compared with animals immunized with BCG, animals immunized with rBCG30-Met-mIFNγ had 0.40 logs fewer CFU in the lung (P=0.003, ANOVA) and 0.46 logs fewer CFU in the spleen (P=0.002, ANOVA). Notably, animals immunized with the recombinant BCG strain expressing intracellular mIFNγ alone (rBCG-Met-mIFNγ) had no increased level of protection over BCG immunized animals in the lung or spleen. Thus, previous predictions that live recombinant vaccines expressing a cytokine alone would result in enhanced protective efficacy did not prove to be correct. Hence, it is the co-expression of both a major pathogen antigen and an immunostimulatory or immunoregulatory cytokine that results in enhanced protection.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the," and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Certain embodiments of this invention are described herein, including the best mode known to the inventors for carrying out the invention. Of course, variations on those embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are individually incorporated by reference herein in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An immunogenic composition for inducing a protective immune response to *Mycobacterium tuberculosis* in a host, the composition comprising:
   a recombinant Bacille Calmette Guérin (rBCG) expressing:
   a 30 kDa *M. tuberculosis* major extracellular protein, wherein said 30 kDa *M. tuberculosis* major extracellular protein is over-expressed and secreted; and
   interferon gamma, wherein said interferon gamma is expressed from an extrachromosomal nucleic acid,
   wherein said 30 kDa *M. tuberculosis* major extracellular protein and said interferon gamma are expressed under the control of a promoter that is not a heat shock promoter.

2. The immunogenic composition according to claim 1 wherein said *M. tuberculosis* major extracellular protein is expressed on an extrachromosomal nucleic acid sequence.

3. The immunogenic composition according to claim 1 wherein said interferon gamma is expressed on an extrachromosomal nucleic acid sequence.

4. The immunogenic composition according to claim 1 wherein said *M. tuberculosis* major extracellular protein and said interferon gamma are expressed from different extrachromosomal nucleic acid sequences.

5. The immunogenic composition according to claim 1 wherein said *M. tuberculosis* major extracellular protein and said interferon gamma are expressed from the same extrachromosomal nucleic acid sequence.

6. The immunogenic composition according to claim 1 wherein said *M. tuberculosis* major extracellular protein is integrated into the rBCG genome under the control of a promoter that is not a heat shock promoter and over-expressed.

7. The immunogenic composition according to claim 1 wherein said interferon gamma is integrated into the rBCG genome under the control of a promoter that is not a heat shock promoter and expressed.

8. The immunogenic composition according to claim 1 wherein said *M. tuberculosis* major extracellular protein and said interferon gamma are integrated into the rBCG genome under the control of a promoter that is not a heat shock promoter and over-expressed.

9. The immunogenic composition according to claim 1 wherein said *M. tuberculosis* major extracellular protein is integrated into the rBCG genome under the control of a promoter that is not a heat shock promoter and over-expressed and said interferon gamma is expressed on an extrachromosomal nucleic acid sequence.

10. The immunogenic composition according to claim 1 wherein said *M. tuberculosis* major extracellular protein is a non-fusion protein.

11. The immunogenic composition according to claim 1 wherein said *M. tuberculosis* major extracellular protein is a fusion protein.

12. The immunogenic composition according to claim 1 wherein said *M. tuberculosis* major extracellular protein is over-expressed and secreted such that a protective immune response is induced in a host.

13. The immunogenic composition according to claim 1 further expressing at least one additional *Mycobacteria* major extracellular protein selected from the group consisting of 12 kDa protein, 14 kDa protein, 16 kDa protein, 23.5 kDa protein, 24 kDa protein, 32A kDa protein, 32B kDa protein, 45 kDa protein, 58 kDa protein, 71 kDa protein, 80 kDa protein, and 110 KD protein.

14. The immunogenic composition according to claim 13 wherein said at least one additional *Mycobacteria* major extracellular protein is from a species of *Mycobacterium* selected from the group consisting of *Mycobacterium tuberculosis; Mycobacterium bovis, mycobacterium leprae*, and *Mycobacterium avium intracellulare.*

15. The immunogenic composition of according to claim 1 wherein said interferon gamma is a covalent dimer comprising one copy of an interferon gamma gene linked to a 19 amino acid peptide linker which is in turn linked to a second copy of an interferon gamma gene.

16. The immunogenic composition according to claim 1 wherein said interferon gamma is expressed in the absence of a signal peptide.

17. The immunogenic composition of claim 1 wherein said rBCG is growth-regulatable.

18. The immunogenic composition of claim 17 wherein said rBCG is siderophore-deficient.

19. A method of inducing a protective immune response to *M. tuberculosis* in a host comprising:

administering the immunogenic composition of claim 1 to said host, wherein a protective immune response to *M. tuberculosis* is induced in said host.

20. The method of claim 19 wherein said host has previously been immunized with a BCG-containing vaccine.

* * * * *